(12) United States Patent
Albertorio et al.

(10) Patent No.: US 11,259,912 B2
(45) Date of Patent: Mar. 1, 2022

(54) ADJUSTABLE SUTURE BUTTON CONSTRUCT

(71) Applicant: ARTHREX, INC., Naples, FL (US)

(72) Inventors: Ricardo Albertorio, Naples, FL (US); Eric S. Zajac, Naples, FL (US); Jacob A. Jolly, Naples, FL (US)

(73) Assignee: ARTHREX, INC., Naples, FL (US)

( * ) Notice: Subject to any disclaimer, the term of this patent is extended or adjusted under 35 U.S.C. 154(b) by 558 days.

(21) Appl. No.: 16/100,420

(22) Filed: Aug. 10, 2018

(65) Prior Publication Data

US 2018/0344447 A1    Dec. 6, 2018

Related U.S. Application Data

(60) Division of application No. 15/640,831, filed on Jul. 3, 2017, now Pat. No. 10,076,407, which is a continuation of application No. 15/599,983, filed on May 19, 2017, now Pat. No. 10,238,484, which is a continuation of application No. 13/908,793, filed on
(Continued)

(51) Int. Cl.
*A61F 2/08* (2006.01)
*A61B 17/04* (2006.01)
*A61B 17/80* (2006.01)
*A61B 17/06* (2006.01)

(52) U.S. Cl.
CPC ........ *A61F 2/0811* (2013.01); *A61B 17/0401* (2013.01); *A61B 17/0487* (2013.01); *A61B 17/8061* (2013.01); *A61B 2017/0403* (2013.01); *A61B 2017/0404* (2013.01); *A61B 2017/0414* (2013.01); *A61B 2017/0496* (2013.01); *A61B 2017/06185* (2013.01); *A61F 2/0805* (2013.01);
(Continued)

(58) Field of Classification Search
CPC ........ A61F 2/08; A61F 2/0811; A61F 2/0847; A61F 2/0852; A61F 2/0858; A61F 2/0864; A61F 2002/0852; A61F 2002/087; A61F 2002/0882; A61B 17/0401; A61B 17/0487; A61B 17/8061; A61B 2017/0403; A61B 2017/0404; A61B 2017/0496; A61B 2017/06185
See application file for complete search history.

(56) References Cited

U.S. PATENT DOCUMENTS 3,176,316 A    4/1965   Bodell
4,187,558 A    2/1980   Dahlen et al.
(Continued)

FOREIGN PATENT DOCUMENTS

EP    0440991 A1    8/1991
EP    1108401 A1    6/2001
(Continued)

*Primary Examiner* — Jerrah Edwards
*Assistant Examiner* — Christine L Nelson
(74) *Attorney, Agent, or Firm* — Carlson, Gaskey & Olds, P.C.

(57) ABSTRACT

An adjustable construct for fixation of a tendon or ligament graft in a tunnel. The construct comprises a flexible, adjustable loop connected to tissue (for example, graft, ligament or tendon). The adjustable loop may be integrated with an additional tissue supporting device (for example, a wedge or a plug). The tissue is secured within a bone socket/tunnel by adjusting the length of the flexible adjustable loop.

18 Claims, 27 Drawing Sheets

Related U.S. Application Data

Jun. 3, 2013, now Pat. No. 9,687,338, which is a division of application No. 12/751,835, filed on Mar. 31, 2010, now Pat. No. 8,460,379.

(60) Provisional application No. 61/311,234, filed on Mar. 5, 2010, provisional application No. 61/311,211, filed on Mar. 5, 2010, provisional application No. 61/259,507, filed on Nov. 9, 2009, provisional application No. 61/168,117, filed on Apr. 9, 2009, provisional application No. 61/165,343, filed on Mar. 31, 2009.

(52) U.S. Cl.
CPC . *A61F 2002/087* (2013.01); *A61F 2002/0852* (2013.01); *A61F 2002/0882* (2013.01)

(56) References Cited

U.S. PATENT DOCUMENTS

| | | | |
|---|---|---|---|
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hiavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,562,669 A | 10/1996 | McGuire |
| 5,575,819 A | 11/1996 | Amis |
| 5,628,756 A | 5/1997 | Barker, Jr. et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck, Jr. et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom, Jr. et al. |
| 6,517,578 B2 | 2/2003 | Hein |
| 6,533,802 B2 * | 3/2003 | Bojarski ............ A61B 17/0401 606/228 |
| 7,097,654 B1 | 8/2006 | Freedland |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,057 B2 | 1/2011 | Cook et al. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 2001/0041938 A1 * | 11/2001 | Hein ..................... A61F 2/0811 623/13.13 |
| 2002/0161439 A1 | 10/2002 | Strobel et al. |
| 2003/0114929 A1 | 6/2003 | Knudsen et al. |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0095130 A1 | 5/2006 | Caborn et al. |
| 2006/0142769 A1 | 6/2006 | Collette |
| 2006/0265064 A1 | 11/2006 | Re et al. |
| 2007/0021839 A1 | 1/2007 | Lowe |
| 2007/0083236 A1 | 4/2007 | Sikora et al. |
| 2007/0118217 A1 | 5/2007 | Brulez et al. |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0046009 A1 | 2/2008 | Albertorio et al. |
| 2008/0051835 A1 | 2/2008 | Mazzocca et al. |
| 2008/0177302 A1 | 7/2008 | Shumas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1 | 3/2009 | Kaiser et al. |
| 2009/0082805 A1 | 3/2009 | Kaiser et al. |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |

(56) References Cited

U.S. PATENT DOCUMENTS

| | | |
|---|---|---|
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |

FOREIGN PATENT DOCUMENTS

| | | |
|---|---|---|
| EP | 1707127 A1 | 10/2006 |
| WO | WO2007002561 A1 | 1/2007 |
| WO | WO2008091690 A1 | 7/2008 |

* cited by examiner

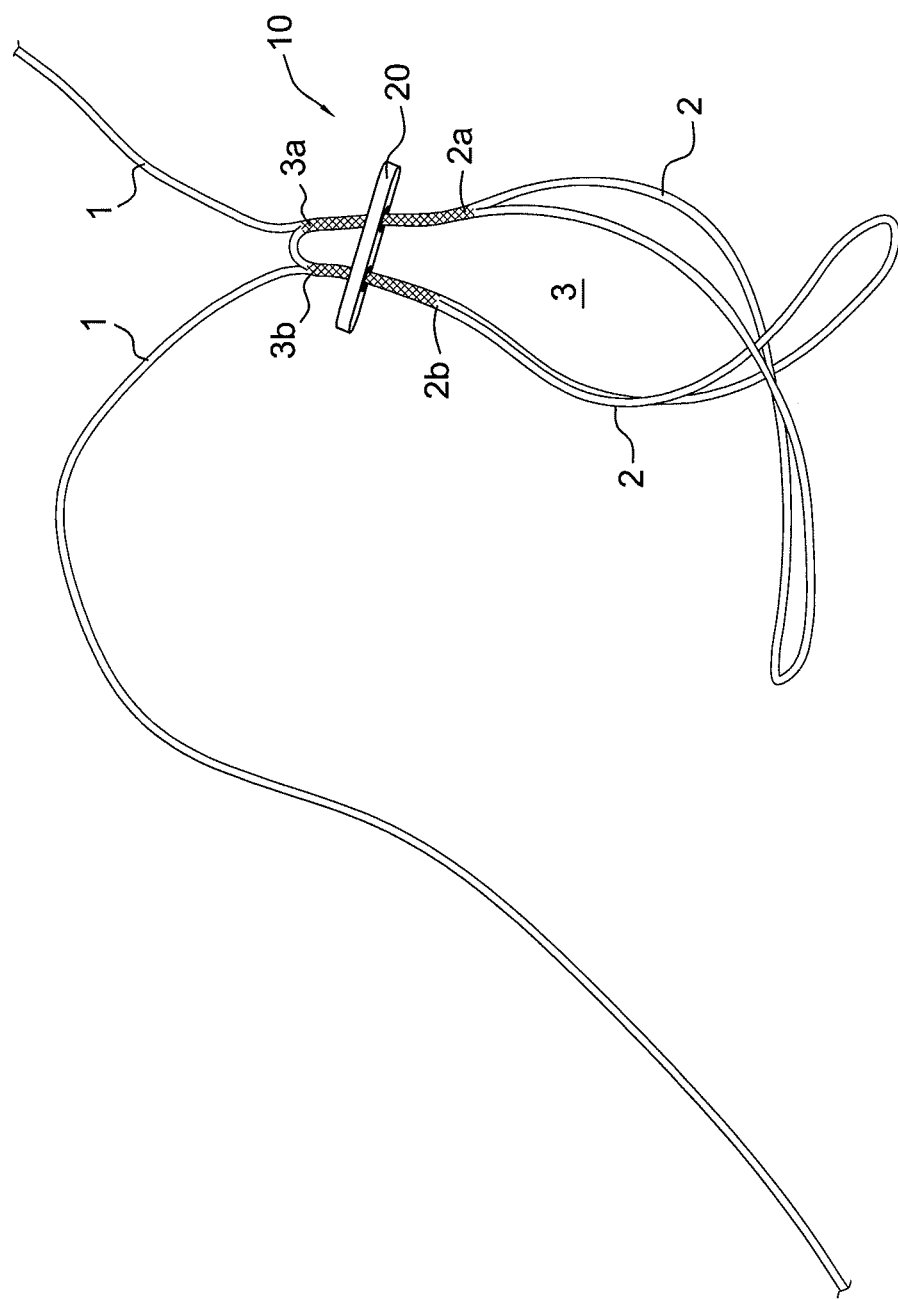

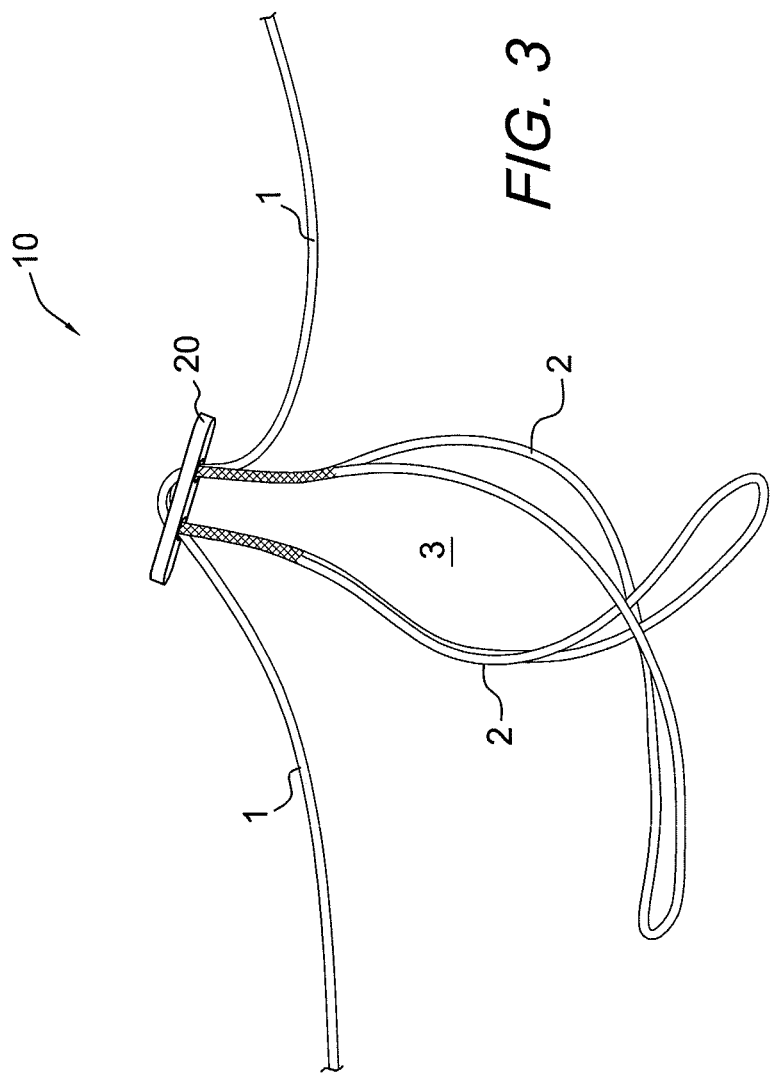

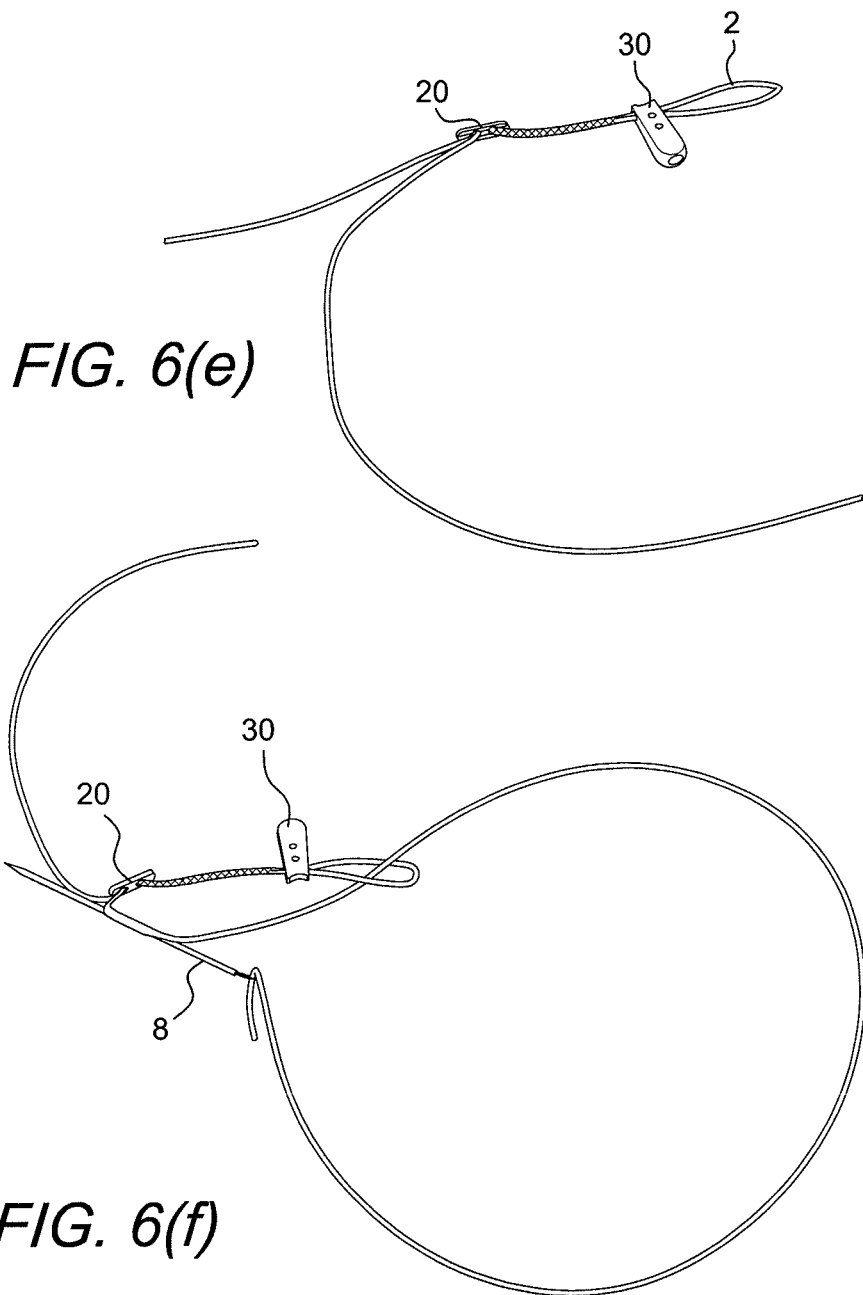
FIG. 6(e)
FIG. 6(f)
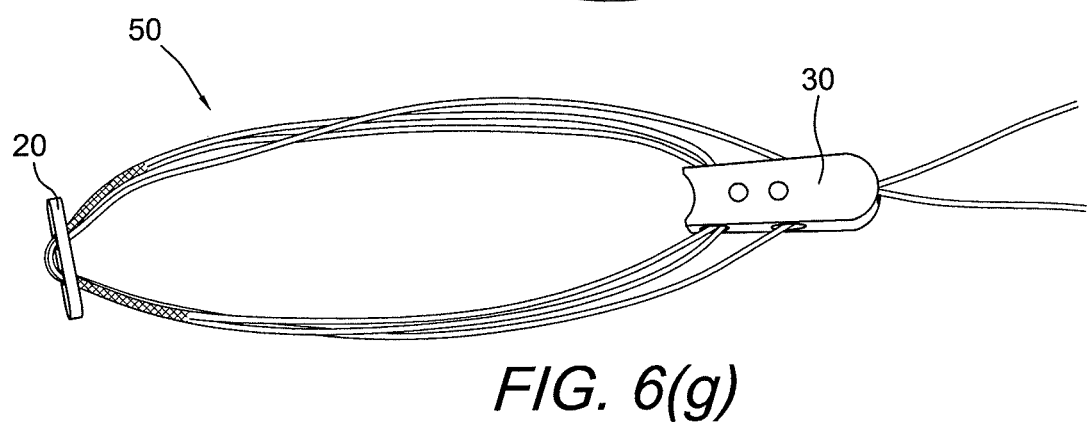
FIG. 6(g)

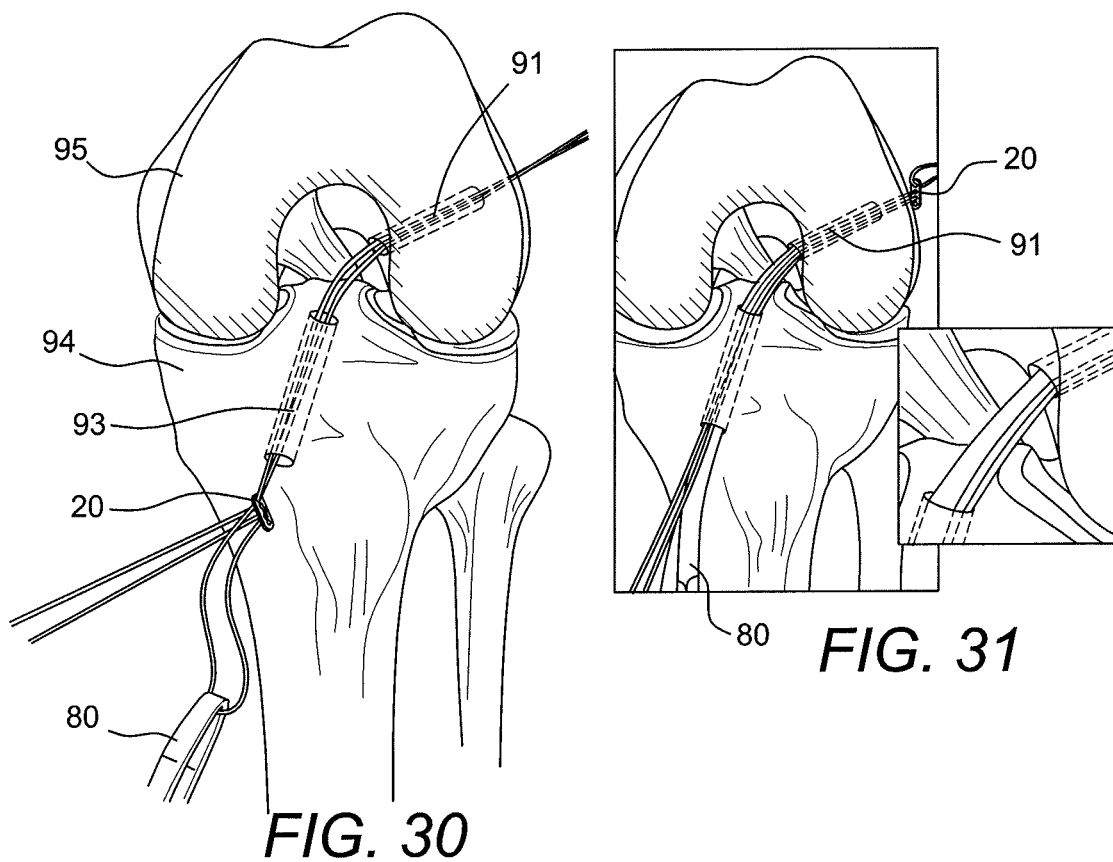
FIG. 30
FIG. 31
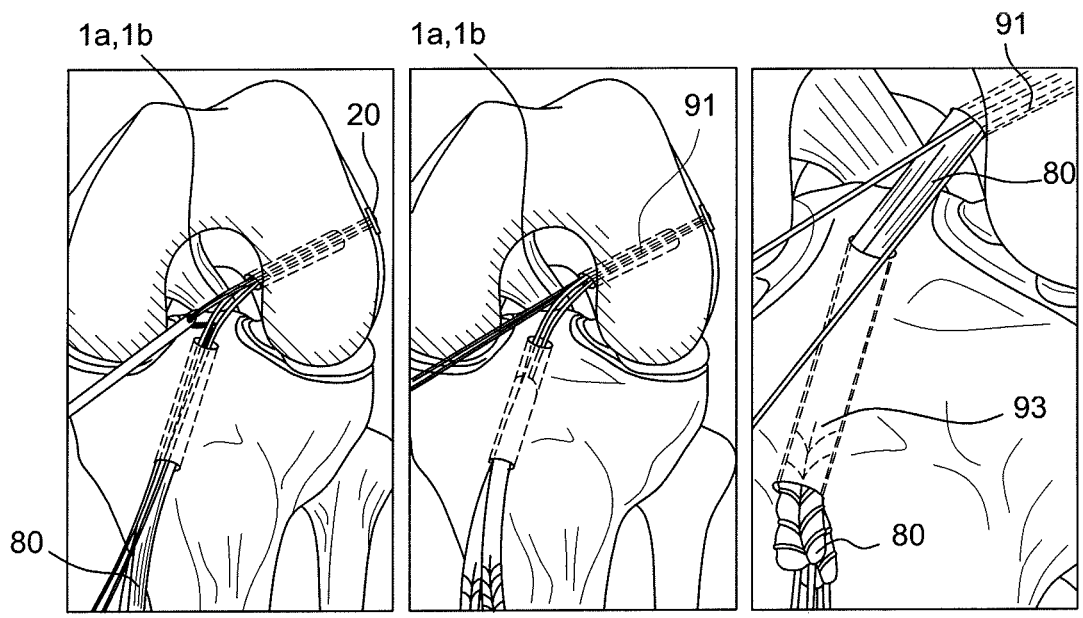
FIG. 32
FIG. 33
FIG. 34

ADJUSTABLE SUTURE BUTTON CONSTRUCT

CROSS-REFERENCE TO RELATED APPLICATIONS

This is a divisional of U.S. patent application Ser. No. 15/640,831, filed Jul. 3, 2017, now U.S. Pat. No. 10,076, 407, which is a continuation of U.S. patent application Ser. No. 15/599,983, filed May 19, 2017, now U.S. Pat. No. 10,238,484, which is a continuation of U.S. patent application Ser. No. 13/908,793, filed Jun. 3, 2013, now U.S. Pat. No. 9,687,338, which is a divisional of application Ser. No. 12/751,835, filed Mar. 31, 2010, now U.S. Pat. No. 8,460, 379, which claims the benefit of U.S. Provisional Application No. 61/165,343, filed Mar. 31, 2009, U.S. Provisional Application No. 61/168,117, filed Apr. 9, 2009, U.S. Provisional Application No. 61/259,507, filed Nov. 9, 2009, U.S. Provisional Patent Application No. 61/311,234, filed Mar. 5, 2010, and U.S. Provisional Patent Application No. 61/311, 211, filed Mar. 5, 2010, the entire disclosures of which are incorporated by reference herein.

FIELD OF THE INVENTION

The present invention relates to the field of surgery reconstruction and, more particularly, to joint or ligament reconstruction techniques and associated fixation and reconstruction devices.

BACKGROUND OF THE INVENTION

Reconstructive surgeries, particularly anterior cruciate ligament (ACL) reconstruction, are well-known in the art. Methods of ACL reconstruction using interference screw fixation are described, for example, in U.S. Pat. Nos. 5,211, 647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like.

Fixation of the graft (for example, a semitendonosus allograft) within the two knee sockets (i.e., the femoral and tibial tunnels or sockets) requires determination of the proper graft length (soft tissue graft or BTB graft) which in turn is calculated based on the entire length of the sockets plus the intraarticular space between them. Proper determination of the graft length ensures accurate placement of the graft within the femoral and tibial tunnels (sockets).

The devices and methods of ligament reconstruction of the present invention provide alternative fixation techniques that employ at least one button with an adjustable suture loop attached to soft tissue, graft or ligament, for improved fixation and exact determination of the graft length within the bone sockets.

SUMMARY OF THE INVENTION

The present invention provides techniques and reconstruction systems for fixation of bone to bone, or soft tissue to bone. The reconstruction system of the present invention comprises at least one button/loop construct with a flexible, adjustable loop connected to tissue (such as soft tissue, graft, tendon, ligament, synthetic material, biological material, bone, or combinations of such materials, among others). The tissue may be directly looped over the flexible, adjustable loop for insertion and fixation into a bone tunnel or socket. Alternatively, the tissue may be looped over a tissue supporting device (such as a wedge, for example) that is connected to the flexible, adjustable loop of the button/loop construct for insertion and fixation into a bone tunnel or socket.

The button/loop construct has an adjustable loop length that allows adjustment in one direction while preventing or locking the construct from loosening in the opposite direction, due to applied tensile forces. The adjustable loop facilitates graft fixation by not requiring calculation of the proper transosseous distance in advance. If a graft supporting device (such as a wedge, for example) is employed, the graft supporting device occludes the socket/tunnel to prevent fluid extravasation and minimizes micromotion of the graft at the bone orifice/graft interface which may lead to tunnel widening. The graft supporting device also provides for both cortical fixation and socket/tunnel compression of the graft or ligament.

The present invention also provides methods of fixation of bone to bone, or soft tissue to bone. An exemplary method of the present invention comprises the steps of: (i) providing a bone tunnel; (ii) providing a button/graft construct including a button and a loop of flexible material having an adjustable length, in the vicinity of the bone tunnel; (iii) looping tissue (graft) over the adjustable loop; (iv) advancing the button/graft construct with the looped tissue through the bone tunnel; and (v) securing the tissue within the bone tunnel by adjusting the length of the adjustable loop.

These and other features and advantages of the invention will be more apparent from the following detailed description that is provided in connection with the accompanying drawing and illustrated exemplary embodiments of the invention.

BRIEF DESCRIPTION OF THE DRAWINGS

FIGS. 1-3 illustrate various view of a button/loop construct with a flexible, adjustable loop according to the present invention (showing the splicing marked with blue and green colors for easy identification).

FIGS. 3(*a*)-(*g*) illustrate exemplary steps of forming/assembling the button/loop construct with a flexible, adjustable loop of FIGS. 1-3 (without a graft supporting device).

FIGS. 3(*h*) and 3(*i*) illustrate a side view and a bottom view, respectively, of an exemplary one-hole button employed in the button/loop construct with a flexible, adjustable loop of the present invention.

FIGS. 6(*a*)-(*g*) illustrate exemplary steps of forming/assembling the button/loop construct with a flexible, adjustable loop (a four-point knotless fixation device and locking mechanism) and with a graft supporting device of FIGS. 4 and 5.

FIGS. 20-40 illustrate subsequent steps of a method of ACL reconstruction according to another embodiment of the present invention and employing the button/loop construct with a flexible, adjustable loop of FIGS. 1-3.

DETAILED DESCRIPTION OF THE PREFERRED EMBODIMENTS

Figure 1:
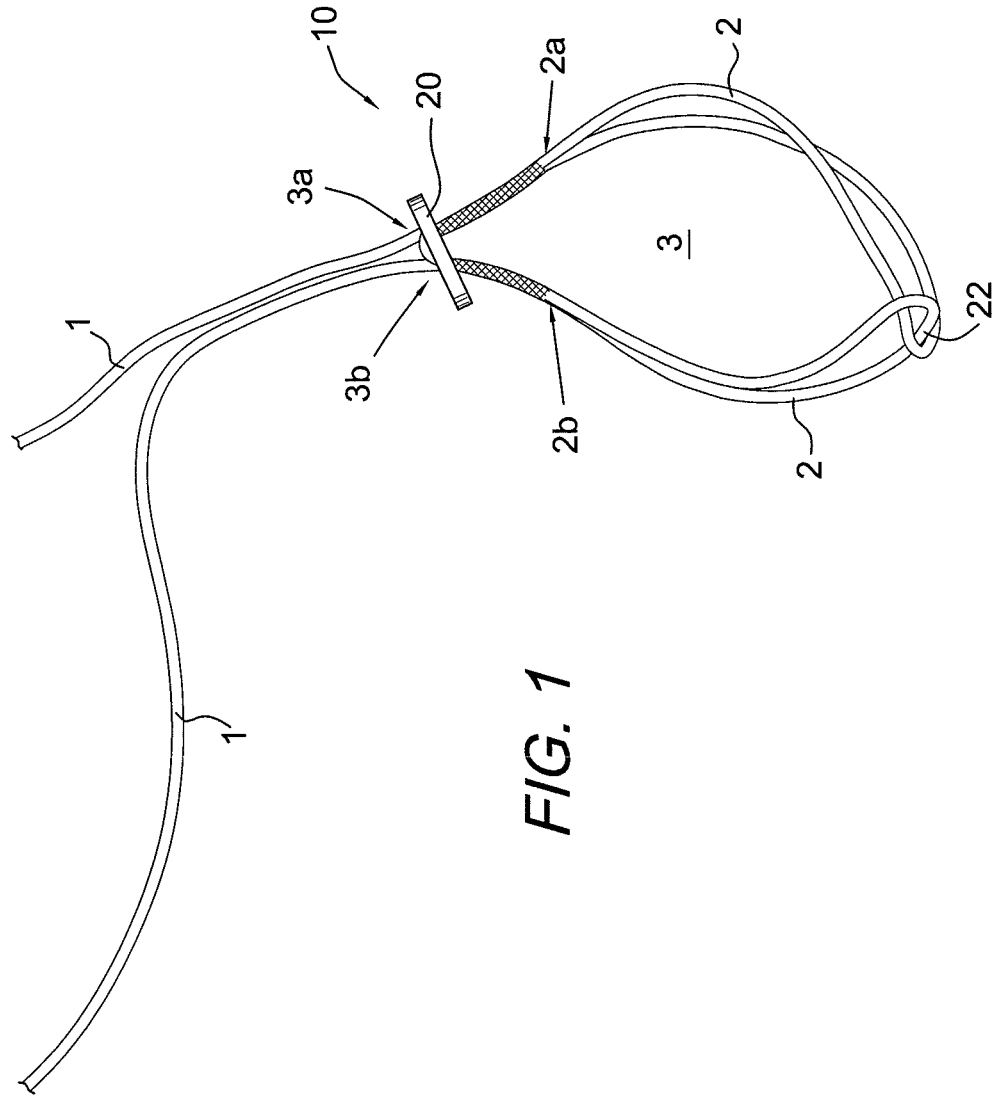

The present invention provides fixation techniques that employ an adjustable suture loop that supports tissue (such as graft or ligament) for improved fixation and elimination for the need to calculate the exact transosseous distance for each bone.

The reconstruction system of the present invention comprises a button/loop construct with a flexible, adjustable loop connected to tissue (for example, soft tissue, graft, tendon, ligament, synthetic material, bone, or combinations of such materials, among others). The tissue may be directly looped over the flexible, adjustable loop for insertion into a bone tunnel or socket. Alternatively, the tissue may be looped over a tissue supporting device (such as a wedge, for example) that is connected to the flexible, adjustable loop for further insertion into a bone tunnel or socket.

The tissue supporting device may or may not incorporate a drive socket for attachment of instrumentation to facilitate orientation or advancement of the device. The adjustable self-locking construct facilitates graft fixation by not necessitating calculation of the proper graft length in advance. The adjustable self-locking construct also provides for both cortical fixation and socket/tunnel compression of the graft or ligament. The tissue supporting device (e.g., the wedge, implant, anchor or plug) also occludes the socket/tunnel to prevent fluid extravasation and minimizes micromotion of the tissue (graft) at the bone orifice/graft interface which may lead to tunnel widening.

The present invention also provides a method of ACL fixation. The method of the present invention comprises the steps of: (i) forming a bone tunnel; (ii) providing a button/graft construct including a button and a loop of flexible material, the loop having an adjustable length; (iii) looping tissue (such as graft or tendon) over the adjustable loop; (iv) advancing the button/graft construct with the looped graft through the bone tunnel; and (v) securing the tissue (graft or tendon) within the bone tunnel by adjusting the length of the adjustable loop.

Referring now to the drawings, where like elements are designated by like reference numerals, FIGS. 1-40 illustrate various components of final assembly 100, 200 of the present invention comprising at least one self-locking adjustable button/loop construct 10 which allows a graft 80 to be fully inserted and seated in femoral and tibial tunnels. The graft may be looped over a graft supporting device 30 (such as a wedge, anchor, or plug), and then inserted and secured within the bone tunnel (as shown in FIGS. 9-19, which illustrate assembly 100 with graft 80 looped over graft supporting device 30 which is attached to adjustable construct 10). Alternatively, the graft may be directly looped through the adjustable loop of the button/loop construct 10 and then inserted and secured within the bone tunnel (as shown in FIGS. 20-40, which illustrate assembly 200 with graft 80 looped directly through the adjustable loop of adjustable construct 10).

FIGS. 1-3 illustrate a button/loop construct 10 of the present invention comprising a flexible, adjustable loop 3 connected to a button 20. The button provides cortical bone fixation of the graft. The loop has an adjustable length (with an adjustable perimeter) and, as described below, may be connected to a tissue supporting device (a wedge) that, in turn, supports tissue (such as a graft or ligament) or may be in direct contact with the tissue. The button/loop construct 10 of the present invention (shown in FIG. 1) is a strong locking mechanism (a four-point knotless locking mechanism) that resists slippage and offers stronger pull-to-failure than anatomical failure load. Specifically, in accordance with the present invention, a graft 80 is looped through the adjustable loop and then pulled into the bone tunnel or, alternatively, is looped over the wedge 30 and positioned within a bone tunnel using a driver which is received in a socket 36 of wedge 30.

Details regarding the formation/assembly of the self-locking adjustable construct 10 (which allows a graft to be fully inserted and seated in a bone tunnel) are provided in U.S. Provisional Patent Application No. 61/259,507 (filed on Nov. 9, 2009) and U.S. Provisional Patent Application No. 61/311,234 (filed on Mar. 5, 2010), the disclosures of which are incorporated by reference in their entirety herewith.

As described in U.S. Provisional Patent Application Nos. 61/259,507 and 61/311,234, a self-locking adjustable knotless construct (such as construct 10 of FIG. 1) consists of button 20 and flexible material 1 with two adjustable eyesplices 2 that are interconnected to form one adjustable loop 3. By pulling on the free braid strands 1, the individual eyesplices 2 constrict and, in turn, reduce the loop length L (FIG. 4) of loop 3. In order for loop 3 to elongate, a force needs to be applied interior to one or both of the eyesplices 2 to elongate the individual loops.

The loop construct 10 of the present invention advantageously (i) eliminates the need to calculate loop length for a loop and button cortical soft tissue fixation anchor; (ii) allows graft tensioning after femoral and tibial fixation have been achieved; (iii) allows self-locking with no surgical knots required; (iv) allows a graft to be fully inserted into a bone tunnel; and (v) eliminates button flipping difficulties in similar fixed loop length fixation systems.

Loop construct 10 comprises two independently-formed and interconnected loops 2, each of the loops 2 having an adjustable length relative to each other. The construct allows adjustment in one direction while preventing or locking the construct 10 from loosening in the opposite direction, due to applied tensile forces.

Flexible strand (braid) 1 is first passed through the button 20 and the strands of the braid are looped around one another. Each end of the braid is spliced through itself, traveling in the direction back towards the original hole passed through in button 20. Each end of the braid is passed through the opposite button hole and down towards interconnected braid loops 2. The final construct 10 with eyesplice interconnection 22 is shown in FIG. 1.

The construct 10 of the present invention advantageously allows unwanted constriction of the loop to be easily reversed when braid strands are pulled in a systematic way; the design also minimizes loop elongation during cyclic loading and supports ultimate loads well above what could be expected when implanted in a patient.

FIG. 3 illustrates another depiction of the button/loop construct 10 of the present invention. As noted above, the button/loop construct 10 consists of two adjustable eyesplices (2) that are interconnected to form one adjustable loop (3). By pulling on the free braid strands (1), the individual eyesplices (2) constrict and, in turn, reduce the loop length of loop (3). In order for loop (3) to elongate, a force needs to be applied interior to one or both of the eyesplices (2) to elongate the individual loops. In a button/loop graft fixation device, the graft would be loaded through loop (3). This method of loading places the load interior to loop (3) but exterior to the individual eyesplices (2), deflecting the load away from either of the adjustable eyesplices preventing their elongation and, thus, preventing elongation of loop (3). This is the basis for the self-locking function.

Exemplary steps of a method of forming/assembling construct 10 of FIGS. 1-3 are detailed in both U.S. Provisional Patent Application Nos. 61/259,507 (filed on Nov. 9, 2009) and 61/311,234 (filed on Mar. 5, 2010), and they include as starting materials a suture strand 1 (for example, 50 inches of braided UHMWPE strand); a suture passing device 8 such as a needle 8 (for example, a blunt tip needle with nitinol loop) and a button 20 (for example, a 3.5 mm titanium button). Exemplary steps of forming/assembling the button/loop construct 10 with a flexible, adjustable loop of FIGS. 1-3 (i.e., the wedgeless device) are illustrated in FIGS. 3(a)-(g) and are detailed below.

Figure 3A:
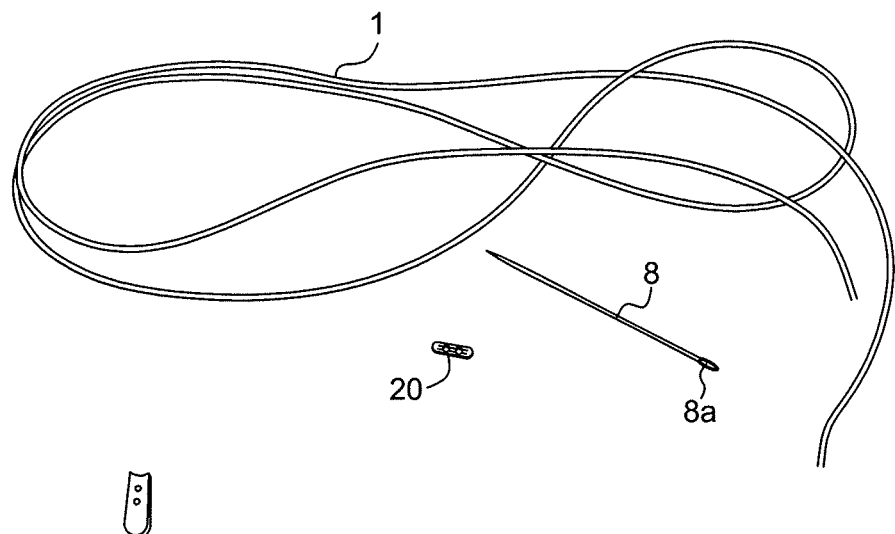

FIG. 3(a) illustrates exemplary starting materials: a suture strand 1 (for example, 50 inches of braided UHMWPE strand); a suture passing device 8 such as a needle 8 (for example, a blunt tip needle with nitinol loop) and a button 20 (for example, a 3.5 mm titanium button).

Figure 3B:
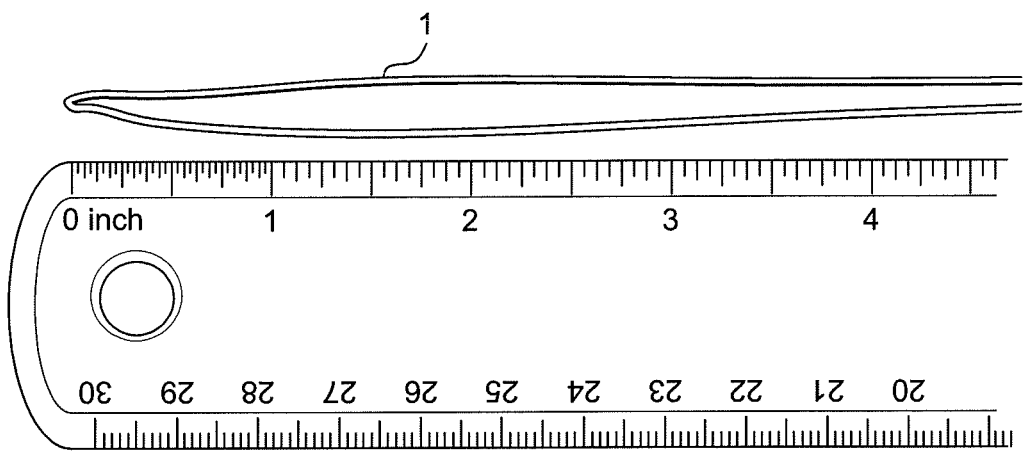
Figure 3C:
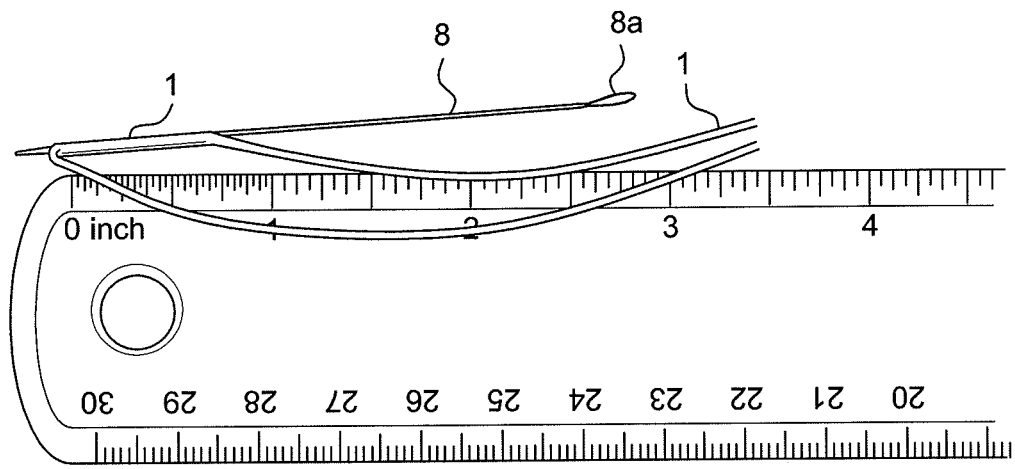
Figure 3D:
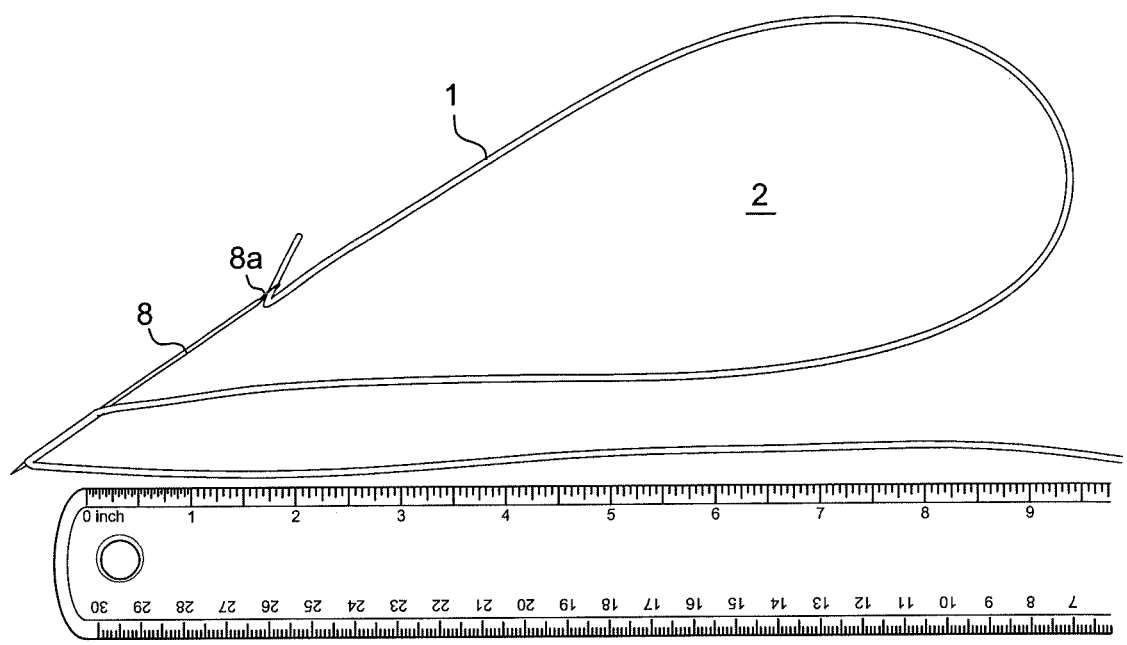

The suture strand 1 is folded to create two equal length parallel braid strands (FIG. 3(b)). At this step, the braid 1 is folded at the midpoint, 25 inches, to create two parallel equal length braid strands (Step 1). At Step 2 (FIG. 3(c)), a first eyesplice 2 is created on the first strand of braid by passing the blunt tip needle through the center of the braid with the end of the braid being carried through in the nitinol loop of the needle. The splice should travel for a distance of about 17-19 mm through the braid towards the braid midpoint created in (Step 1) (FIG. 3(d)).

Figure 3E:
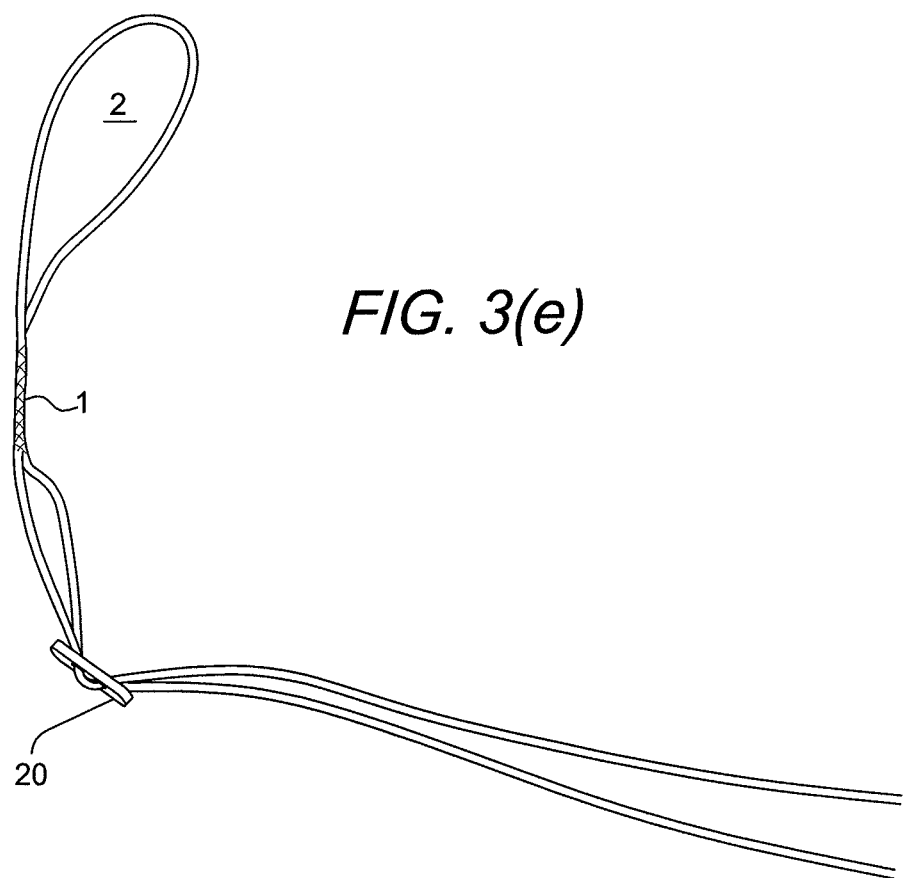
Figure 3F:
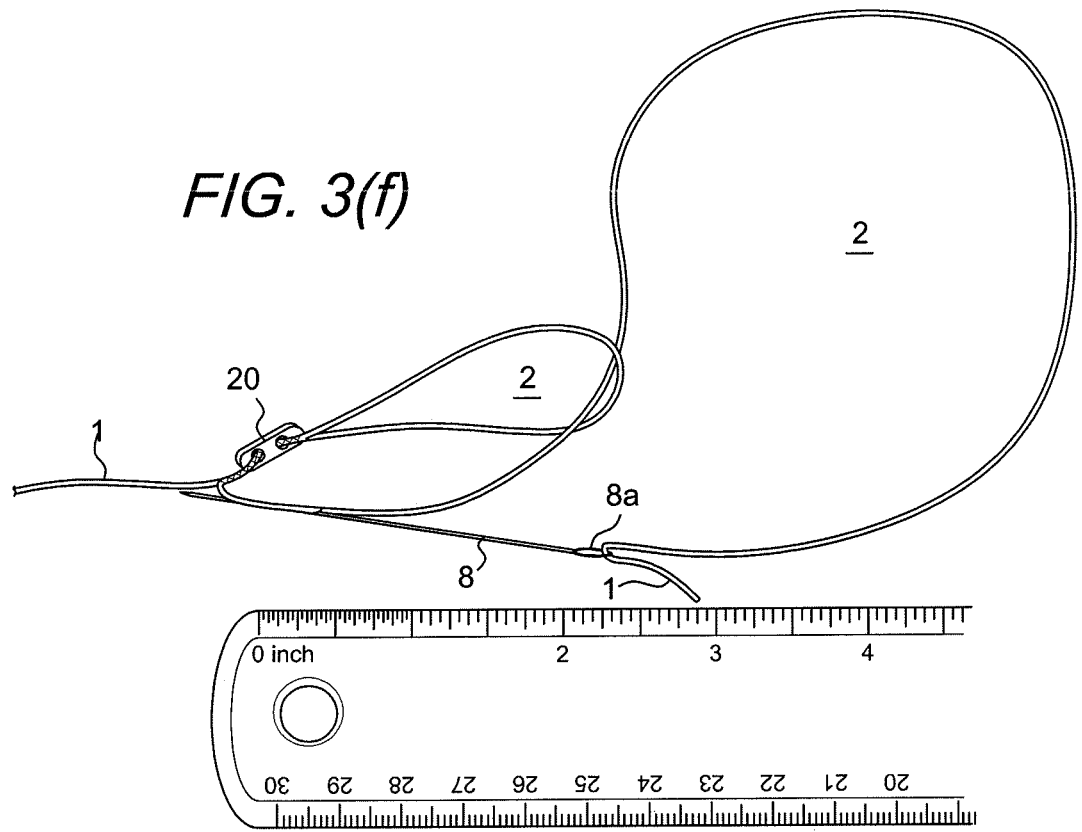

Once the first eyesplice 2 has been formed, at Step 3, the button 20 is slid over the non-spliced strand passing the strand through both button holes (FIG. 3(e)). The button is slid so that it rests over the first spliced section. At Step 4, a second eyesplice 2 is formed, similar to the first one, with the opposing strand (FIG. 3(f)). The strand should be looped through the first eyesplice loop resulting in two eyesplice loops that are interconnected. Again, the splice length should be between 17-19 mm. The splice should be created such that the exiting aperture of the splice is as close as possible to the first eyesplice.

Figure 3G:
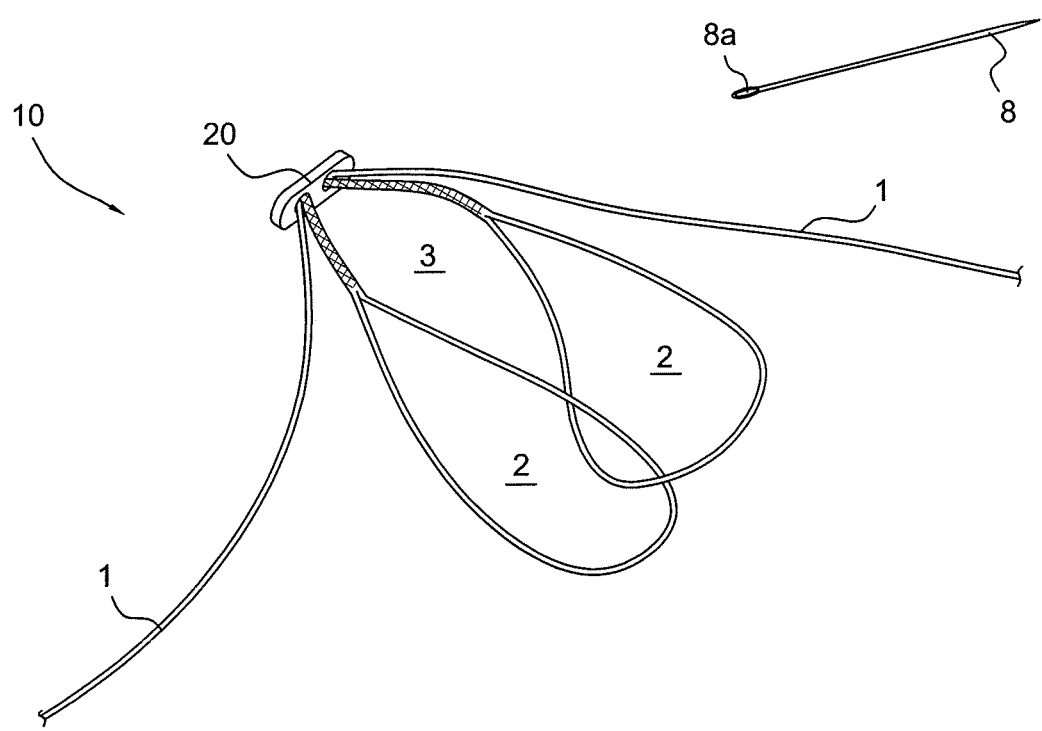

At Step 5, once the free end has created the eyesplice, pass it through both holes of the button and slide the button to center between the two eyesplice sections (FIG. 3(g)). The result is one overall adjustable loop 3 that is comprised of the interconnected adjustable eyesplice loops 2 (FIG. 3(g)).

FIG. 1 illustrates free strands 1 of the self-locking adjustable construct 10 pulled back through the button 20 to expose the splice exits points 3a, 3b. Also shown in FIG. 1 are two splice entrance points 2a, 2b. FIG. 2 shows the button 20 adjusted downward to give full view of the two splice entrance points 2a, 2b and the two splice exit points 3a, 3b. FIG. 3 illustrates the final self-locking adjustable construct 10 with no additional splicing occurring and with the free strands 1 passed through the opposite button holes of the button 20.

The button 20 may be formed, for example, of metal, PEEK or PLLA. The flexible material 1 may be suture such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others). The flexible material 1 may also contain a bioabsorbable material, such as PLLA or one of the other polylactides, for example, and/or may be formed of twisted fibers having strands of a contrasting color added to the braided threads, to make the suture more visible during surgical procedures. In exemplary embodiments, flexible material 1 may be a braided suture cover containing strands of a high strength suture material, such as FiberWire® suture, sold by Arthrex, Inc. of Naples, Fla. If desired, the flexible material 1 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, pliability, handleability or abrasion resistance, for example.

Figure 3H:
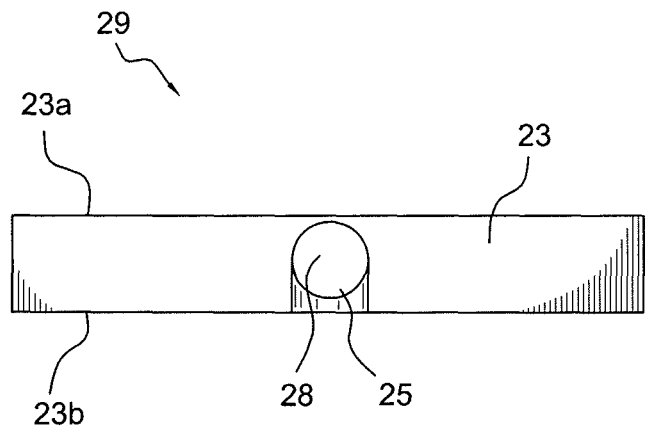
Figure 3I:
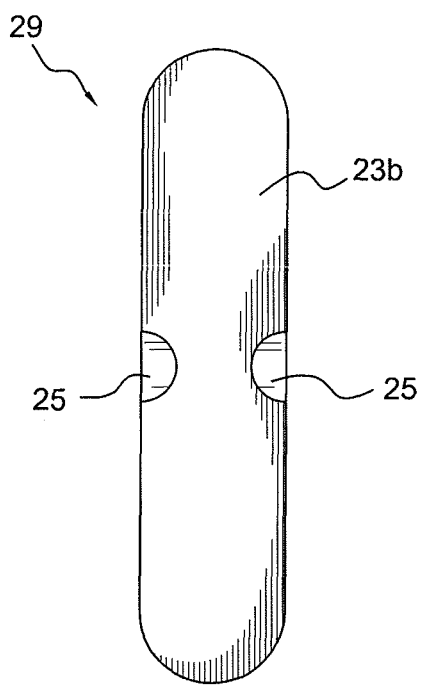

Details of button 20 are set forth in U.S. Patent Publ. No. 2007/0179531 (Thornes), the disclosure of which is also incorporated by reference in its entirety herewith. As detailed in U.S. Patent Publ. No. 2007/0179531, the button 20 is provided with at least one opening that allows the passage of the flexible material 1 to pass thereto. The button may be round or oblong and may be provided with one or more apertures. An exemplary and illustrative embodiment of a button 29 that may be employed in the self-locking adjustable construct 10 of the present invention (in both the wedge and the wedgeless embodiments) is illustrated in FIGS. 3(h) and 3(i). Button 29 is a one-hole button comprising an oval body 23 with a first or top surface 23a and a second or bottom surface 23b opposite to the first or top surface 23a. A plurality of apertures 25 are provided within the body 23 and a through-hole 28 extends within the body 23. The through-hole 28 is adjacent the bottom surface 23b, and communicates with the apertures 25. In this manner, the flexible material 1 may be passed through the one hole 28 of the button 29 during the formation/assembling of the self-locking adjustable construct 10 of the present invention.

Figure 4:
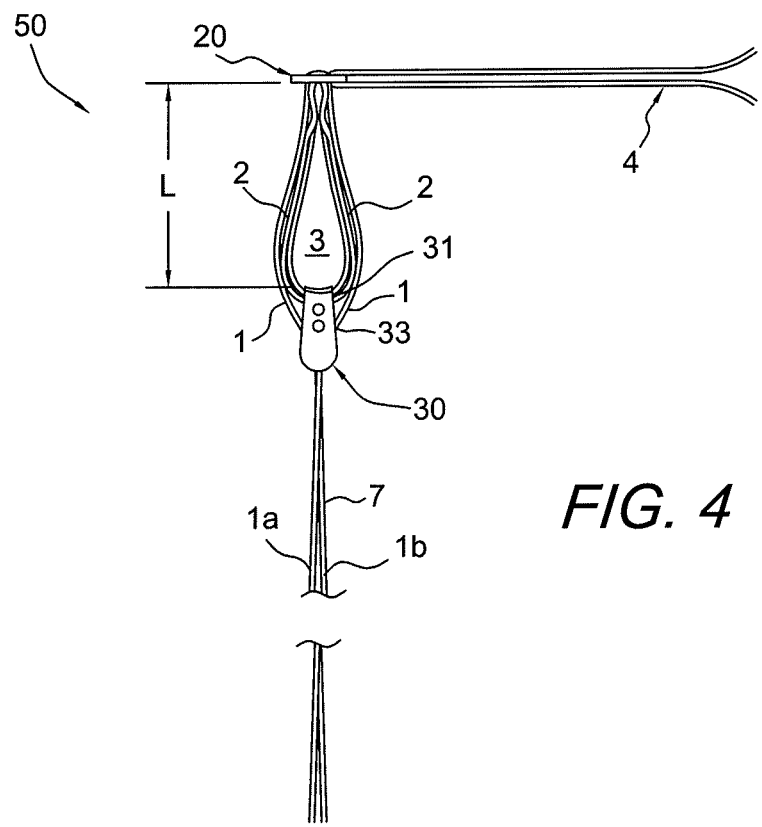
FIG. 4 illustrates a side view of the adjustable button/loop construct of FIGS. 1-3 integrated with a graft supporting device (for example, a wedge) according to a first embodiment of the present invention.
Figure 5:
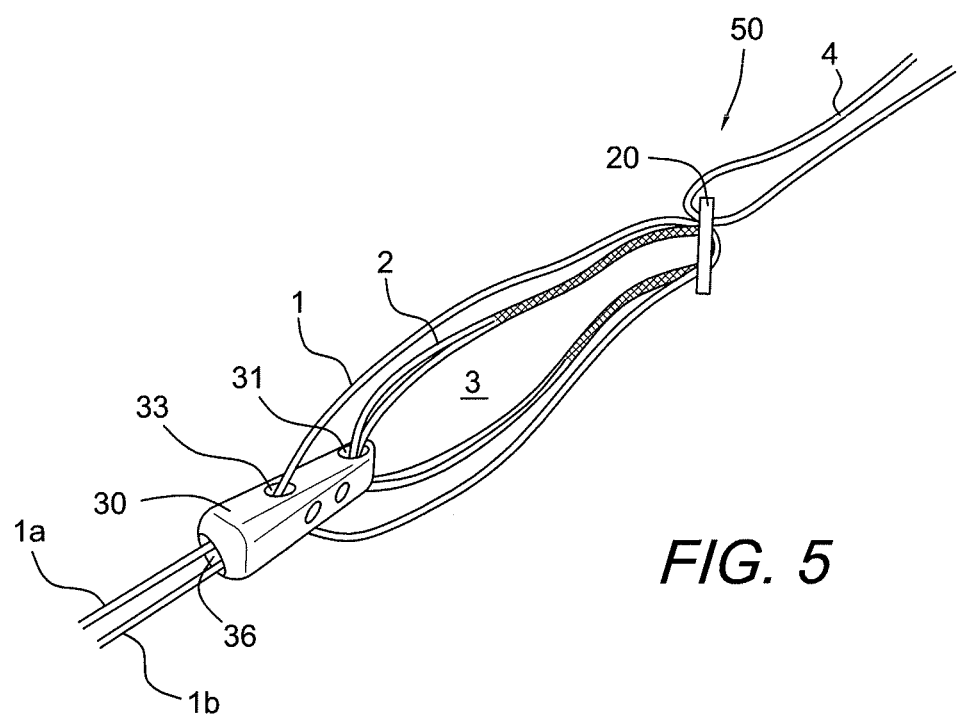
FIG. 5 illustrates a perspective view of the assembly of FIG. 4.
Figure 6:
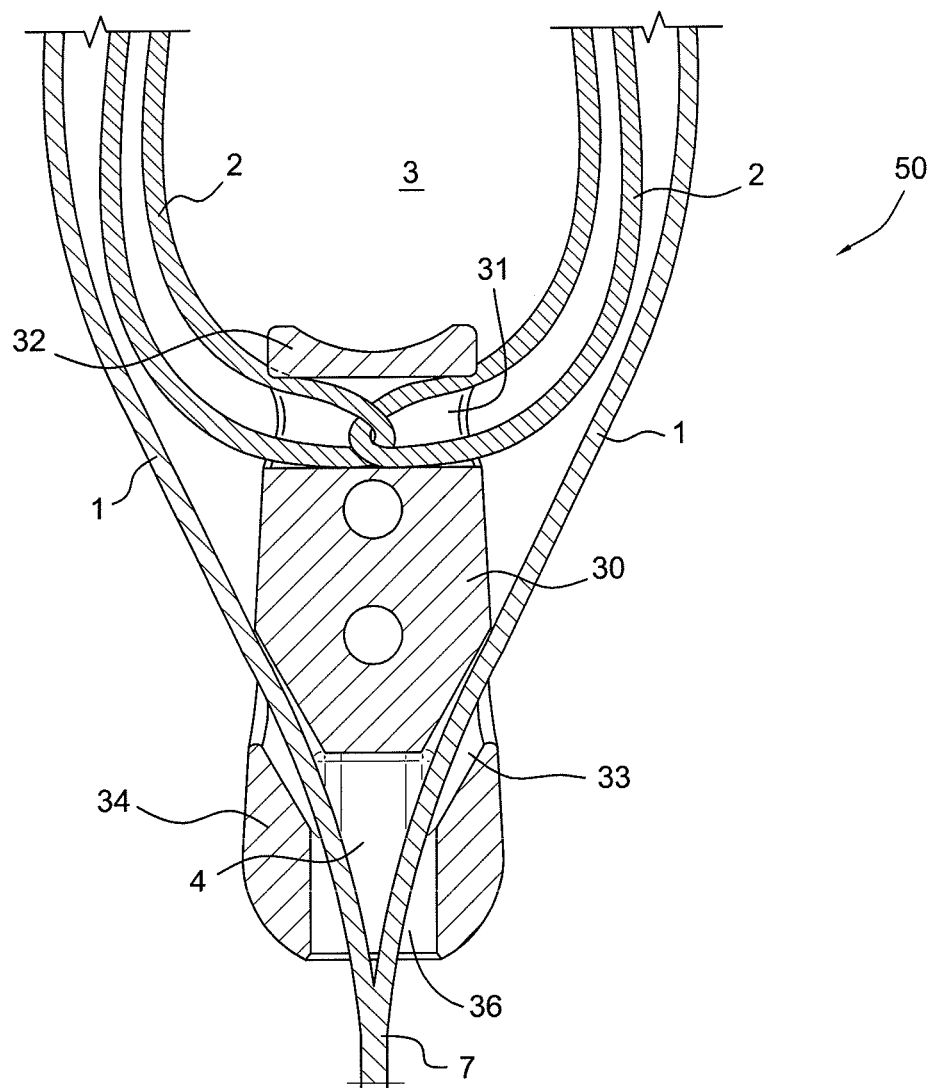
FIG. 6 illustrates a partial, cross-sectional view of the wedge of the assembly of FIG. 5, showing how the suture construct sits in the wedge.

FIGS. 4-6 illustrate the construct of FIG. 1 with a graft supporting device 30 attached thereto. The graft supporting device may be a wedge, an anchor, a plug or an implant, among others. If a wedge is employed, the wedge 30 may have a trapezoidal shape (as shown in FIGS. 4-7) or similar shapes, and is provided with a plurality of transversal passages or through holes 31, 33 (FIGS. 4-6) that allow flexible strand 1 of construct 10 to pass therethrough. Opening 36 (FIGS. 5 and 6) is also provided at a most distal end of the wedge 30 to receive a corresponding end of a driver.

Details of a method of attaching the self-locking adjustable construct 10 of FIGS. 1-3 to graft supporting device 30 (for example, a wedge 30) to form assembly 50 are set forth in U.S. Provisional Patent Application No. 61/311,211 (filed on Mar. 5, 2010), the disclosure of which is incorporated by reference herewith in its entirety. As detailed in U.S. Provisional Patent Application No. 61/311,211, the eyesplice is passed through the proximal hole 31 of the wedge 30. After the formation of the second eyesplice, the wedge 30 is positioned between the button 20 (or button 29) and eyesplice interconnection 22 (FIG. 1). Once the free end has created the eyesplice, it is passed through both holes of the button and the button is slid to center between the two eyesplice sections. The result is one overall adjustable loop that is comprised of the interconnected adjustable eyesplice loops. For the wedge assembly, the assembly is finished by moving the wedge 30 such that the wedge is positioned over the eyesplice interconnection 22 and the free braid strands 1 are passed through the side holes of the wedge and out of the distal opening 36 (distal hex socket) of wedge 30.

FIGS. 6(a)-(g) illustrate exemplary steps (Steps 1-7) of forming/assembling assembly 50 having the button/loop construct with a flexible, adjustable loop (a four-point knotless fixation device and locking mechanism) and the graft supporting device 30 of FIGS. 4 and 5.

Figure 6A:
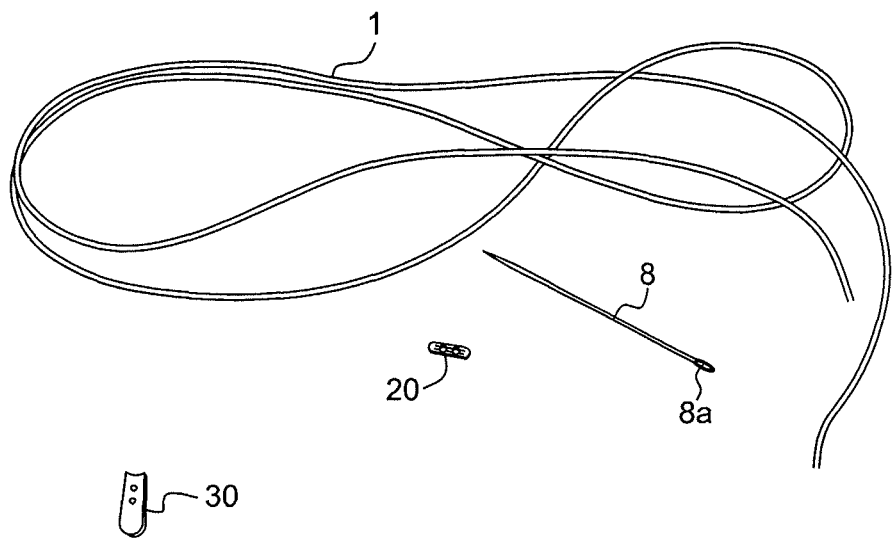

FIG. 6(a) illustrates starting materials: suture strand 1 (for example, 50 inches of braided UHMWPE strand); a suture passing device such as a needle 8 (for example, a blunt tip needle with nitinol loop); a button 20, 29 (for example, a 3.5 mm titanium button); and a wedge 30 (for example, a PEEK femoral wedge for wedge assemblies).

Figure 6B:
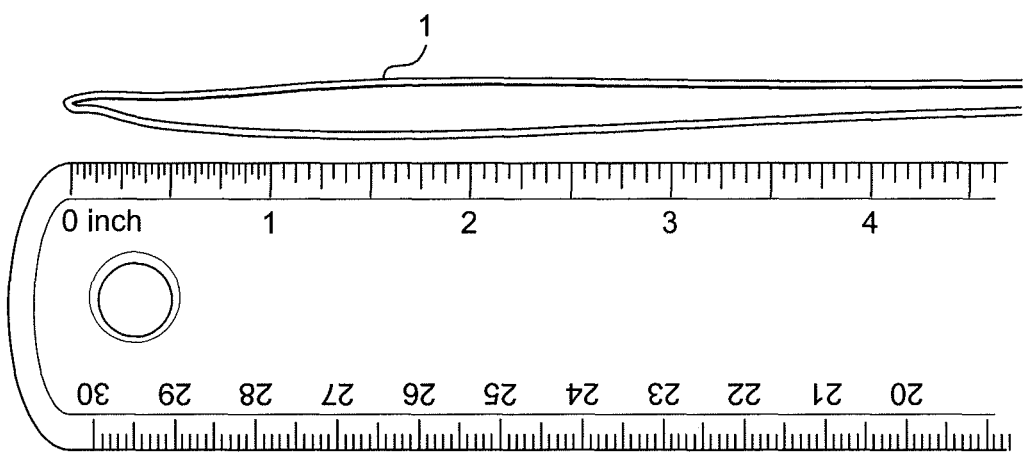

FIG. 6(b) illustrates the suture strand 1 folded to create two equal length parallel braid strands. At this step, the braid 1 is folded at the midpoint, 25 inches, to create two parallel equal length braid strands (Step 1).

Figure 6C:
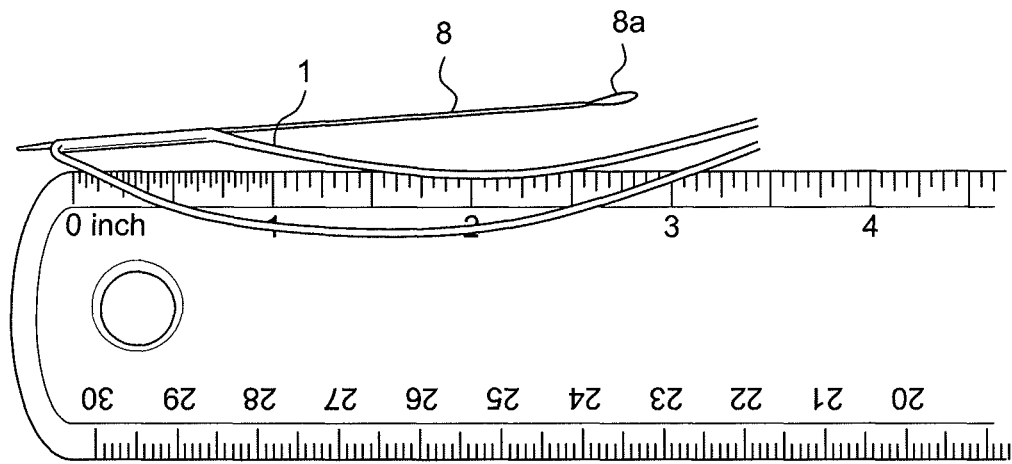

FIG. 6(c) shows the measurement of the eyesplice. At this step (Step 2), an eyesplice 2 is created on the first strand of braid 1 by passing the blunt tip needle 8 through the center of the braid 1 with the end of the braid being carried through in the nitinol loop of the needle 8. The splice should travel for a distance of about 17-19 mm through the braid towards the braid midpoint created in Step 1.

Figure 6D:
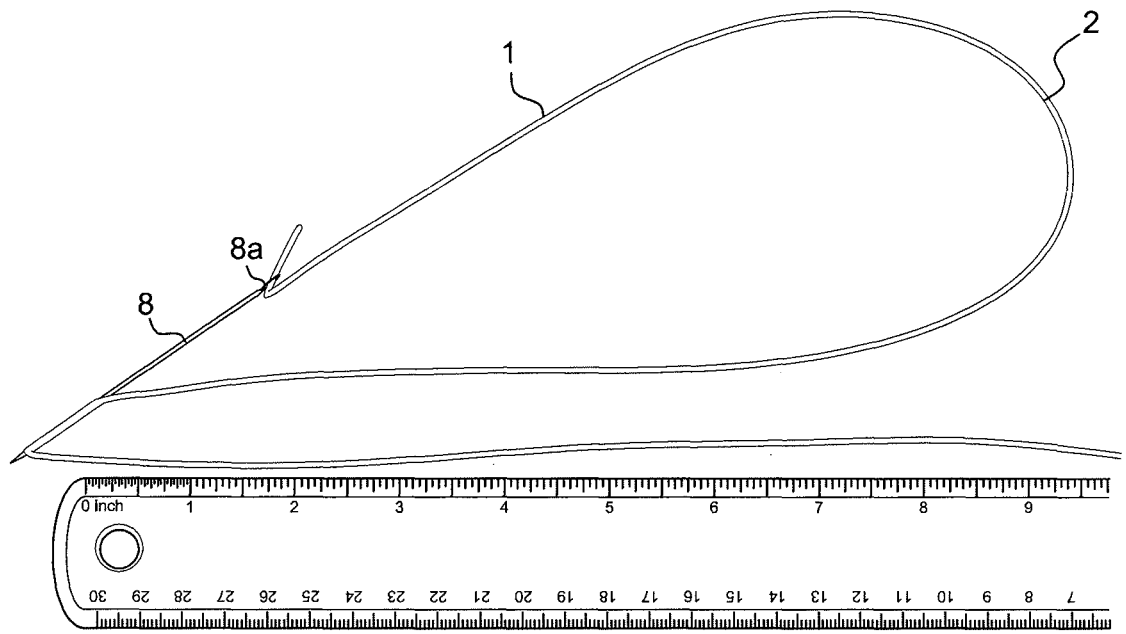

FIG. 6(d) shows the braid carried though the splice 1 with the nitinol loop needle 8.

FIG. 6(e) shows the formation of the first eyesplice 2. Step 3: the button is slid over the non-spliced strand passing the strand through both button holes. Also pass the free strand that results from the eyesplice through the button holes. Slide the button so that it rests over the first spliced section. For the wedge assembly, additionally, pass the eyesplice through the proximal hole of the wedge.

FIG. 6(f) shows the formation of the second eyesplice. Step 4: create another eyesplice 2 similar to the first one, with the opposing strand. The strand should be looped through the first eyesplice loop resulting in two eyesplice loops that are interconnected. Again, the splice length should be between 17-19 mm. The splice should be created such that the exiting aperture of the splice is as close as possible to the first eyesplice. On wedge assembling, the wedge 30 should be positioned between the button 20 and eyesplice interconnection 22 as shown in FIG. 6(f).

FIG. 6(g) shows the final braid construct assembly 50. Step 5: once the free end has created the eyesplice, pass it through both holes of the button 20 and slide the button to center between the two eyesplice sections 2. The result is one overall adjustable loop 3 that is comprised of the interconnected adjustable eyesplice loops 2. For the wedge assembly, finish the assembly by moving the wedge 30 such that is positioned over the eyesplice interconnection 22 and pass the free braid strands through the side holes of the wedge and out of the distal hex.

Step 6: After the loop is constructed, the loop may be stretched for approximately 30 seconds at 50 LBF. The force to stretch the loop is preferably applied such that it acts on the overall loop created between the two eyesplices rather than either individual eyesplice loop.

Step 7: Place passing suture through button hole and pull until strands are equal length.

Figure 7:
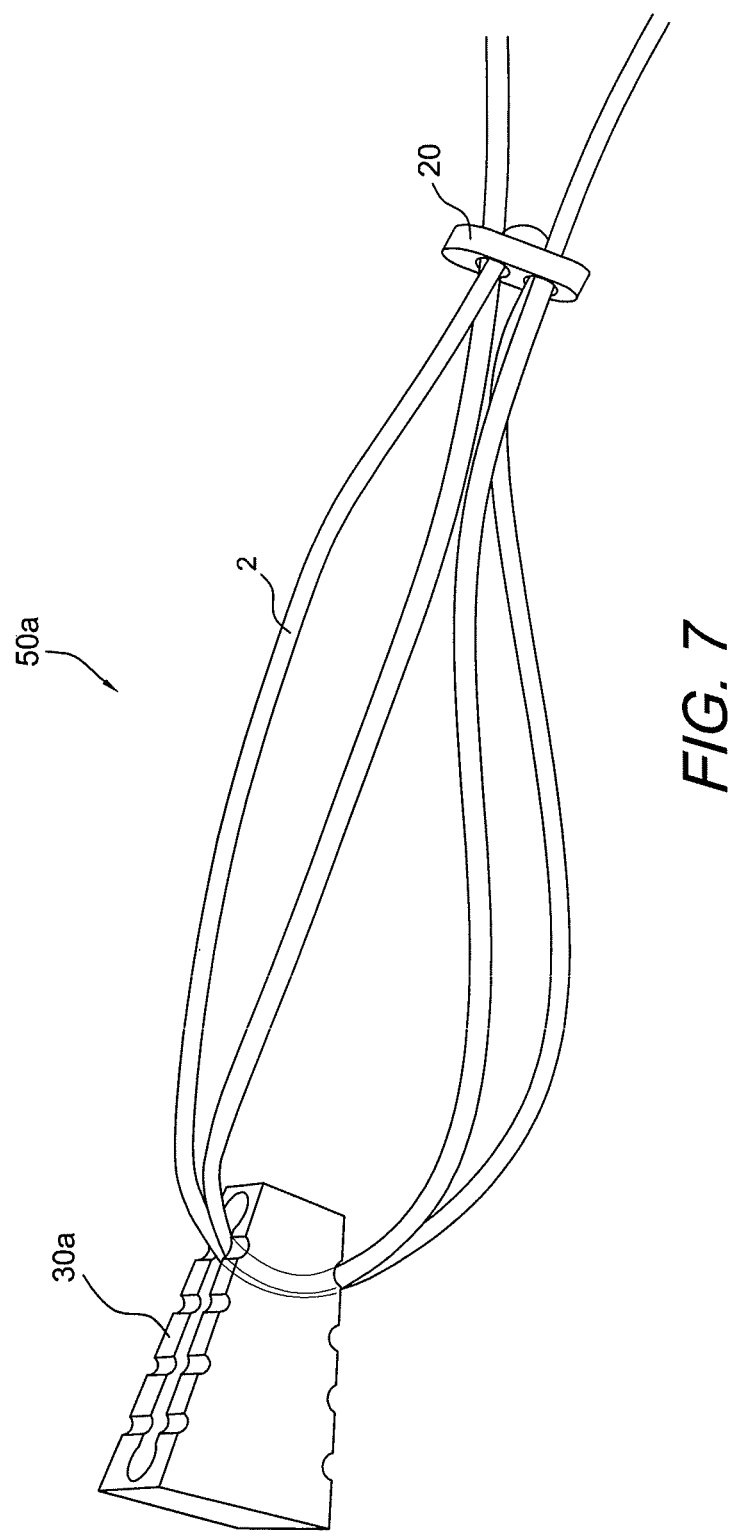
FIG. 7 illustrates a perspective view of the adjustable button/loop construct of FIGS. 1-3 integrated with another graft supporting device (for example, a trapezoidal wedge) according to a second embodiment of the present invention.
Figure 8:
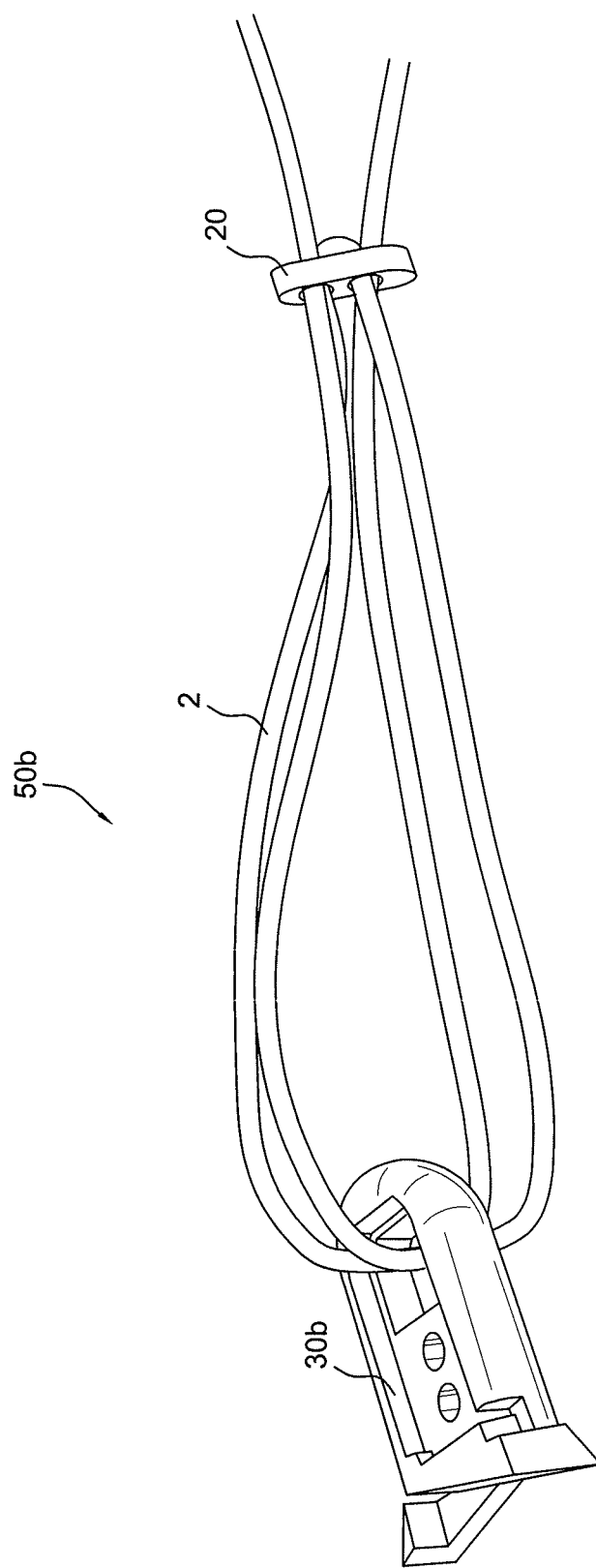
FIG. 8 illustrates a perspective view of the adjustable button/loop construct of FIGS. 1-3 integrated with another graft supporting device (for example, an expanding plug) according to a third embodiment of the present invention.

FIGS. 7 and 8 illustrate assemblies 50a, 50b including the self-locking adjustable construct 10 of FIGS. 1-3 attached to other graft supporting devices such as supporting device 30a (FIG. 7) or plug 30b (FIG. 8) which are similar to the graft supporting device 30. As detailed below, supporting devices 30, 30a, 30b are employed for preparing and securing soft tissue, graft or ligament within bone tunnels, according to embodiments of the present invention. In additional embodiments, some of the supporting devices may be also provided with fixation features (such as threads, ridges, or expanding tabs, for example) to aid in the fixation of the tissue (graft or ligament) within the bone tunnel or socket. For example, a graft supporting device which may also act as a fixation device is plug 30b, which may be an expanding plug, the details of which are set forth in U.S. Patent Publ. No. 2008/0275554, the disclosure of which is incorporated by reference in its entirety herewith.

Figure 17:
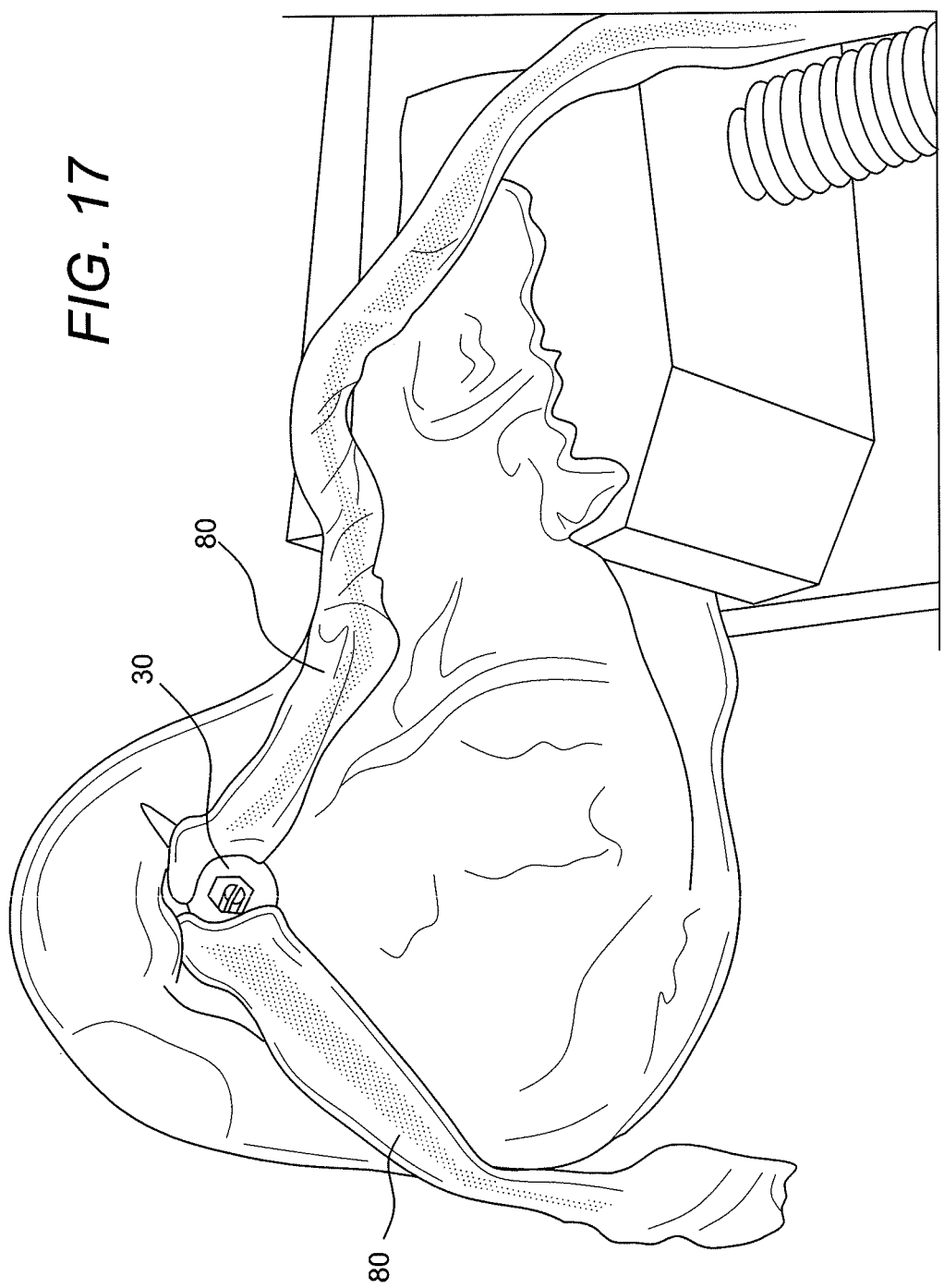
Figure 18:
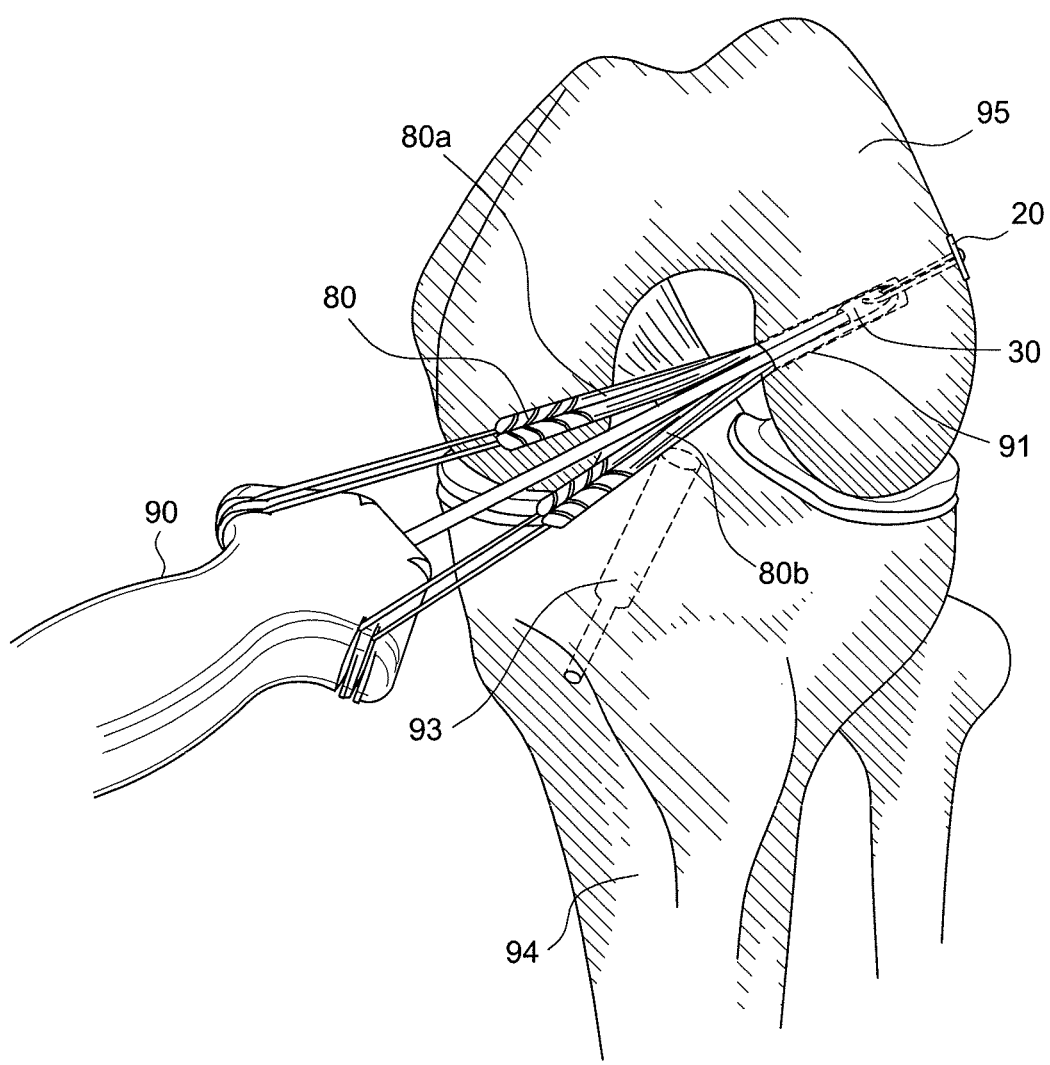
FIG. 18 illustrates a driver securing the assembly of FIG. 9 within a femoral tunnel or socket.
Figure 19:
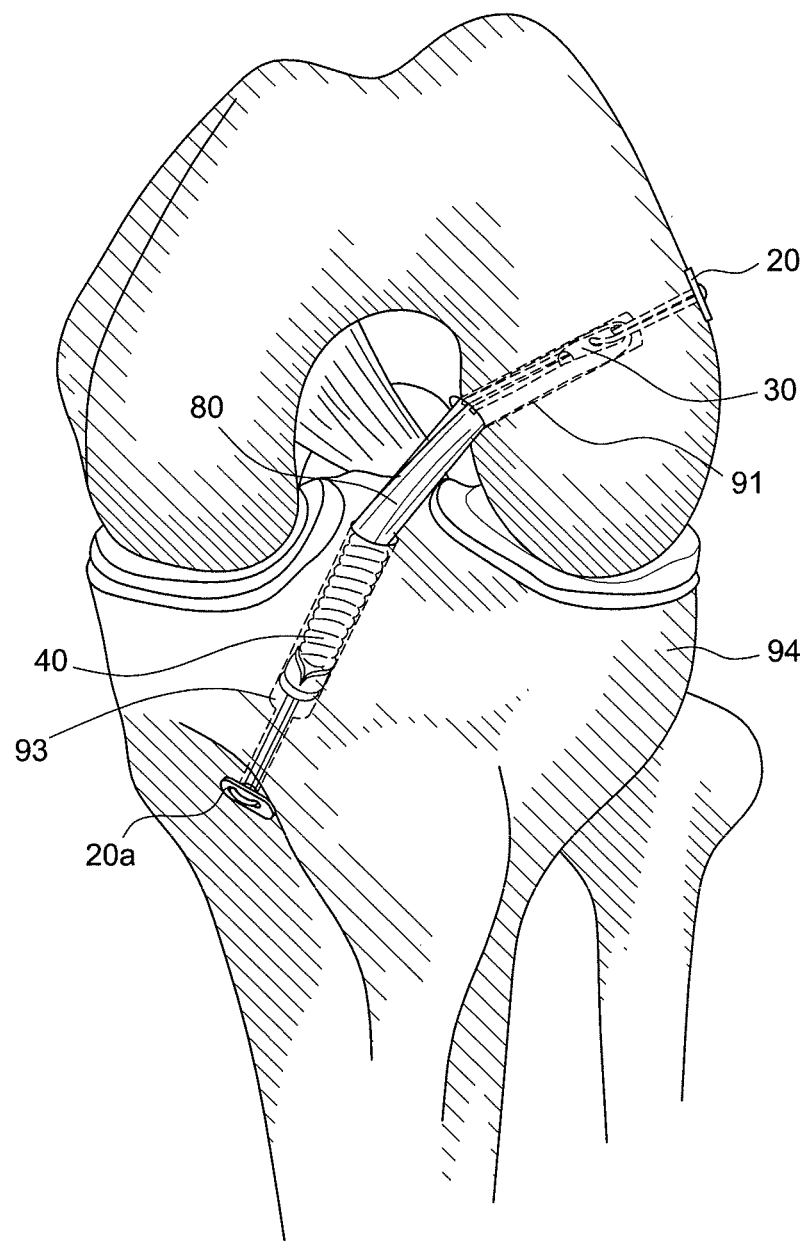
FIG. 19 illustrates the assembly of FIG. 9 secured within both the femoral tunnel and the tibial tunnel.

FIGS. 9-19 illustrate assembly 100 (button/wedge/adjustable loop assembly 100) comprising a self-locking adjustable knotless construct 10 (formed of button 20 and two adjustable eyesplices (2) that are interconnected to form one adjustable loop (3)) and a graft supporting device 30 (for example, a femoral wedge 30) with tissue 80 (graft, tendon, ligament, synthetic material, biologic material, bone, or combinations of such materials) attached thereto. The flexible loop of the self-locking adjustable knotless construct 10 is connected to graft supporting device 30. FIG. 19 illustrates final assembly 100 of the present invention positioned within the femoral and tibial sockets/tunnels and according to a method of ACL reconstruction of the present invention.

Figure 9:
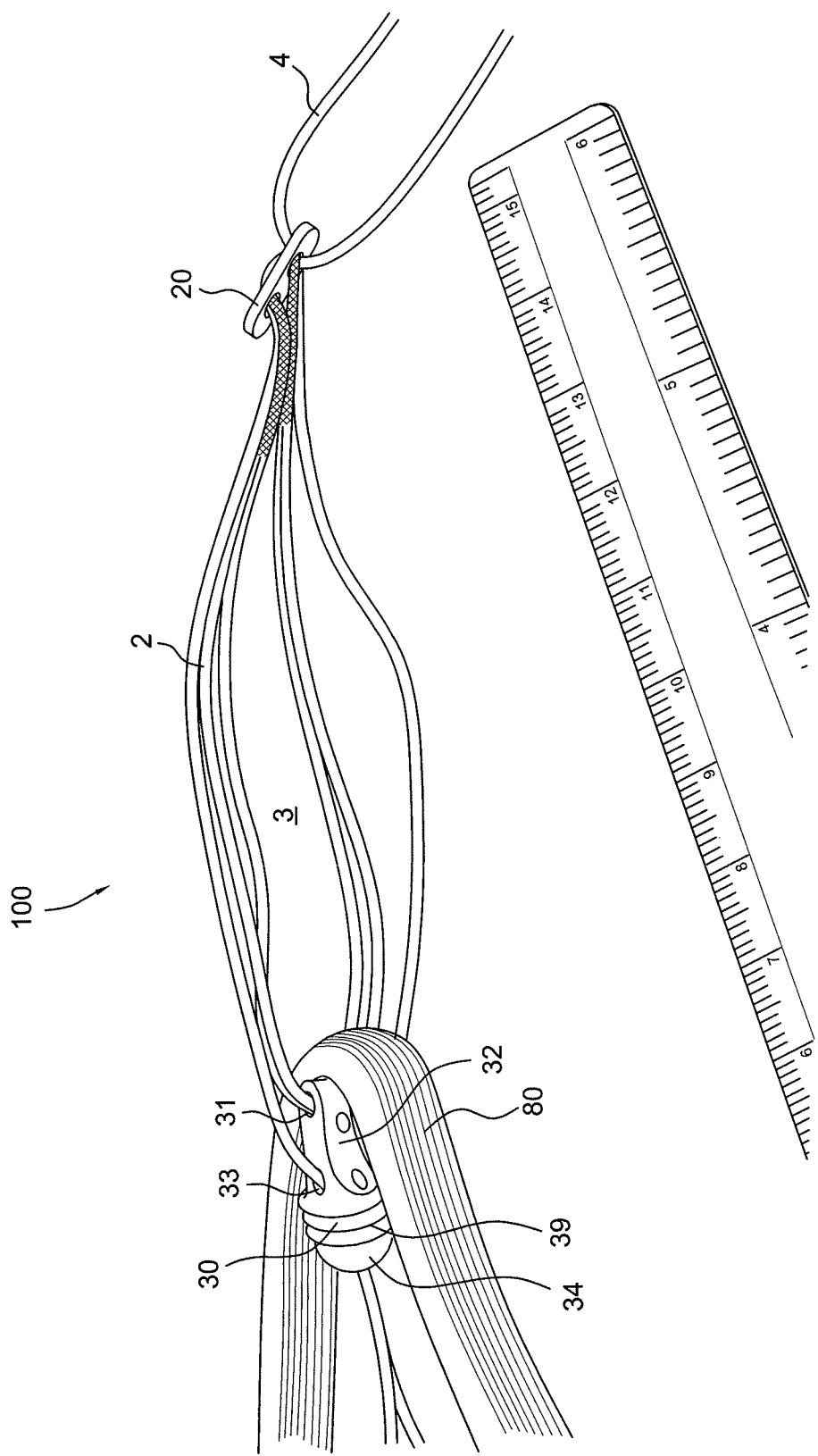
FIG. 9 illustrates the assembly of FIG. 4 (including an adjustable button/loop construct with a graft supporting device) and further provided with tissue (a graft or ligament, for example) looped over the graft supporting device.

As shown in FIG. 9, tissue (graft) 80 is placed through the open loop of the self-locking adjustable knotless construct 10 and rests over the wedge "saddle" 30. The tissue 80 may be a ligament graft such as autograft, allograft or artificial graft. The loop is connected to button 20 and to the graft supporting device 30.

The graft supporting device 30 shown in FIGS. 6 and 9 has a proximal end 32 and a distal end 34. In an exemplary embodiment, the proximal end 32 is shaped like a saddle and the distal end 34 is shaped like a cylindrical plug. The proximal end 32 contacts the graft 80 and has a shape and surface suitable for protecting the graft. The distal end 34 separates the graft bundle and compresses the graft 80 against the walls of the tunnel or socket after insertion providing additional fixation. The outer surface of the distal end 34 may have additional features 39 such as threads, ridges, or expanding tabs (FIG. 9) designed to aid in fixation. One skilled in the art will recognize that many shapes and surface features will aid in protecting the graft and provide additional fixation.

The graft supporting device 30 also includes a passageway 31 for connecting to the flexible loop. Additionally, the graft supporting device 30 may be provided with a second passageway 33 for connecting to the ends of the flexible loop. Second passageway 33 may connect to opening 36 extending from the distal end 34 of the graft supporting device 30. Opening 36 provides a channel for the ends 1a, 1b (FIG. 6) of the flexible loop to extend out from the surgical site for adjusting the tension and size of the loop.

Opening 36 may also be shaped to mate with an insertion instrument (for example, a driver).

The reconstruction system 100 may be provided as pre-assembled and/or pre-packaged to the surgeon, or may be assembled by the surgeon during the surgery. If the surgeon is using an autograft, after the surgeon harvests the graft, the graft 80 is attached to the reconstruction system 100 by sliding the graft through the loop 3 and over the proximal end 32 of the graft supporting device 30. The entire reconstruction system is ready for implantation once the graft has been looped over the graft supporting device. If desired, the graft 80 may be secured to the graft supporting device with sutures, for example.

Figure 10:
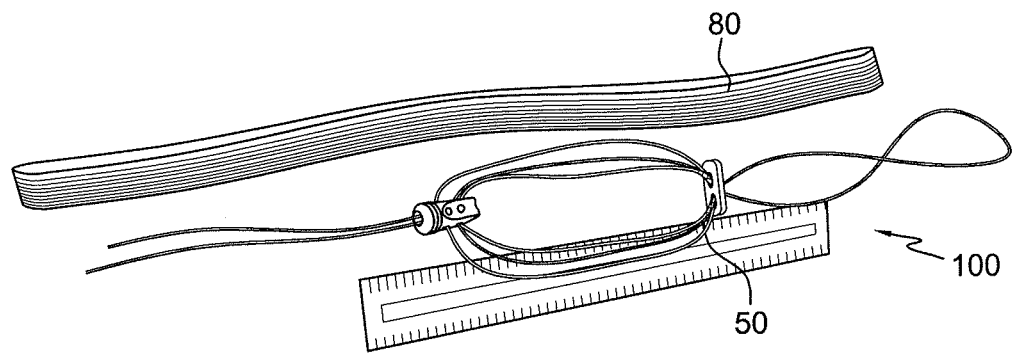
FIGS. 10-17 illustrate subsequent steps of a method of tissue reconstruction according to an embodiment of the present invention and employing the assembly of FIG. 9.
Figure 11:
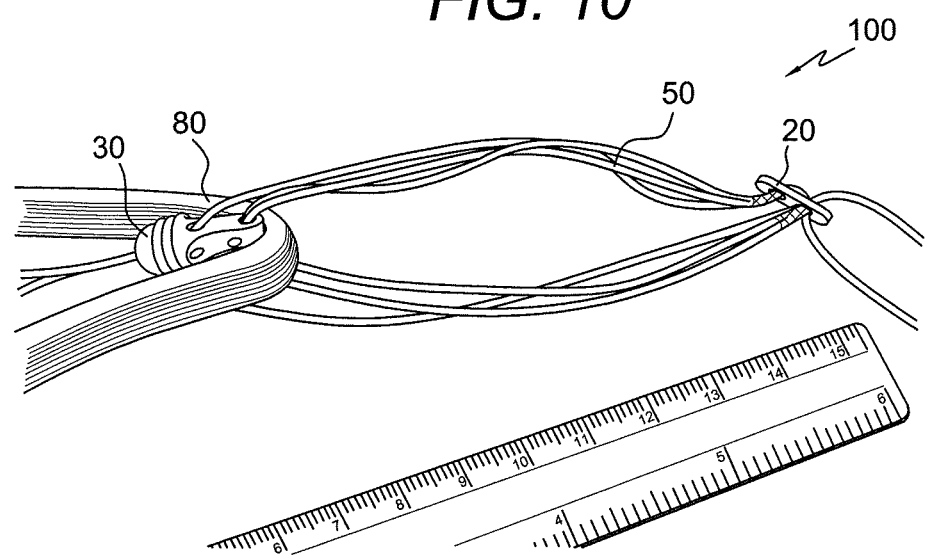

FIGS. 10-17 illustrate various steps of a method of preparing and inserting the reconstruction system 100 of FIG. 9 to bone 15, according to an exemplary embodiment of the present invention. FIG. 10 illustrates tissue (graft) 80 prior to looping it through the adjustable loop of the construct 50, while FIG. 11 illustrates the tissue (graft) 80 after the looping through the adjustable loop (and over graft supporting device 30) of the construct 50.

Figure 12:
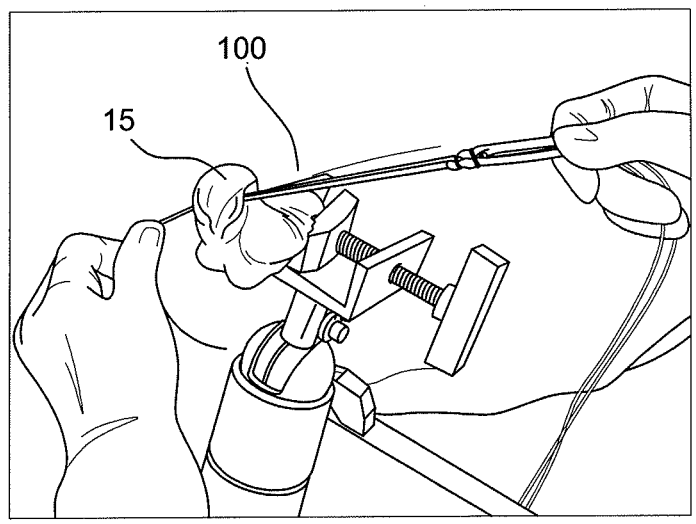
Figure 13:
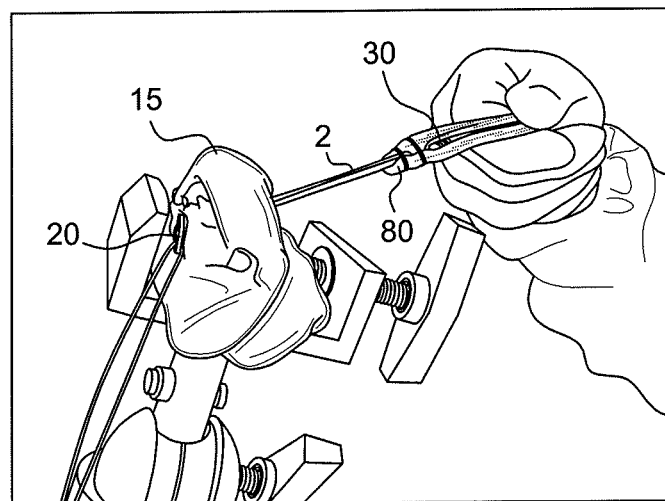
Figure 14:
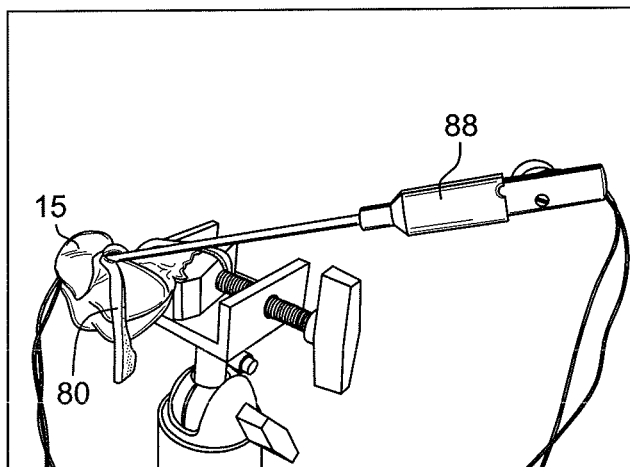
Figure 15:
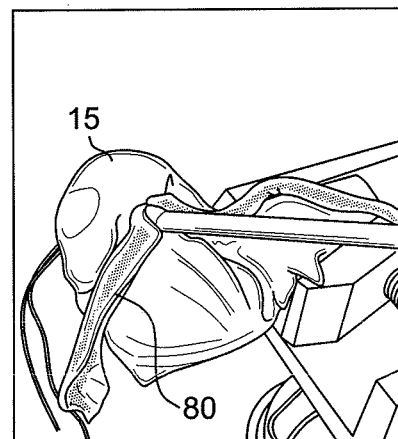
Figure 16:
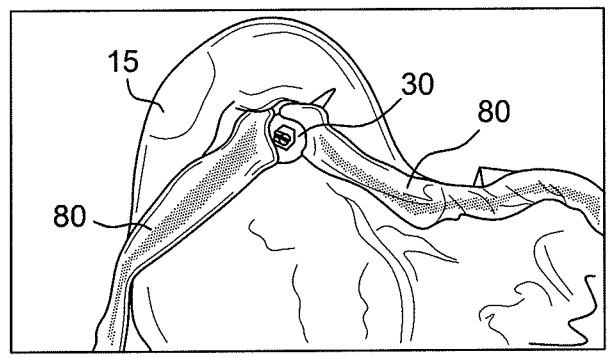

FIG. 12 illustrates the reconstruction system 100 being introduced into a tunnel in the femoral side of the knee (usually through an arthroscopic portal). The button 20 is pulled out of the bone cortex with the passing sutures (later discarded) and self-flips onto the cortex once tension is released on the passing suture (FIG. 13). FIG. 14 illustrates the adjustable flexible loop 3 being shortened by applying tension to the ends 1a, 1b of the loop 3 exiting the graft supporting device 30. FIGS. 14 and 15 show further tensioning of the ends 1a, 1b of the loop utilizing an instrument 88 (such as a suture tensioner, for example). As the length L of the loop 3 is shortened by pulling on the ends, the graft supporting device 30 is advanced further into the tunnel between the graft. FIG. 16 shows the graft supporting device 30 in place within the tunnel, separating the graft bundles, and imparting graft compression against the tunnel walls and occluding the tunnel entrance. FIG. 17 is an enlarged view of the construct of FIG. 16. FIGS. 18 and 19 illustrate additional exemplary views of the assembly 100 inserted and fixated within the femoral tunnel and the tibial tunnel.

Preferably, the graft supporting device (wedge) 30 is flush with the opening of the femoral socket and with the graft bundles separated at the socket orifice. For this, the wedge 30 is not pulled all the way into the socket, but rather is positioned at the opening of the bone socket and flush with the opening. The double bundle technique of the present invention facilitates strong, adjustable cortical fixation with aperture graft compression, anatomic (double bundle) graft orientation within a single socket, and easy graft insertion and positioning with preloaded driver.

Femoral socket 91 (shown in FIGS. 18 and 19) may be drilled transtibially through the medial portal or by a retrograde technique using an Arthrex FlipCutter®, disclosed in U.S. Patent Application Publication No. 2009/0275950. In a Medial Portal Option, for medial portal and transtibial drilling, an Arthrex RetroButton® Drill Pin may be used. The intraosseous distance is noted by pulling back on the pin by hand, until it catches the femoral cortex. The depth marking are read on the pin closest to the femoral notch.

The femoral socket 91 is drilled to a depth about equal to the amount of graft desired in the femoral socket, using a low profile reamer, for example. After creating tibial tunnel 93, the passing suture is brought through tibia 94.

If using the FlipCutter®, the intraosseous length off the Drill Sleeve is read. The femur 95 is drilled (by retrograde drilling) a depth equal to the amount of graft desired in the femoral socket 91 (as detailed in the FlipCutter® technique). After creating the tibial tunnel 93, the passing suture is brought through the tibia 94.

As shown in FIG. 18, the double bundle construct 100 is then loaded with graft 80 looped over the wedge 30 and positioned on driver 90 which is inserted into opening 36 of wedge 30 (FIG. 6).

The passing suture is passed through the tibia 94 and out the femur 95. The button 20 is positioned so that the nonlooped side is facing lateral. The button 20 is pulled through the femur 95 until it exits the lateral cortex to achieve fixation. This is indicated when the mark on the loop reaches the femoral socket opening. It is important to note that no tension should be put on the loop shortening strands until the button 20 has been passed, self-flips, and is fully seated against the cortex, as this could compromise graft advancement.

The marked loop shortening strands are retrieved from the implant through the medial portal. The graft 80 is advanced and tension is pulled on the loop shortening strands. The graft will be completely seated when the mark on the graft reaches the femoral socket 91. The wedge 30 is flush with the opening of the femoral socket 91 and with graft bundles 80a, 80b separated, as shown in FIGS. 18 and 19. Tibial fixation is achieved by known methods in the art, for example, by employing an interference device 40 (for example, an interference screw 40) and another button 20a (FIG. 19).

Figure 20:
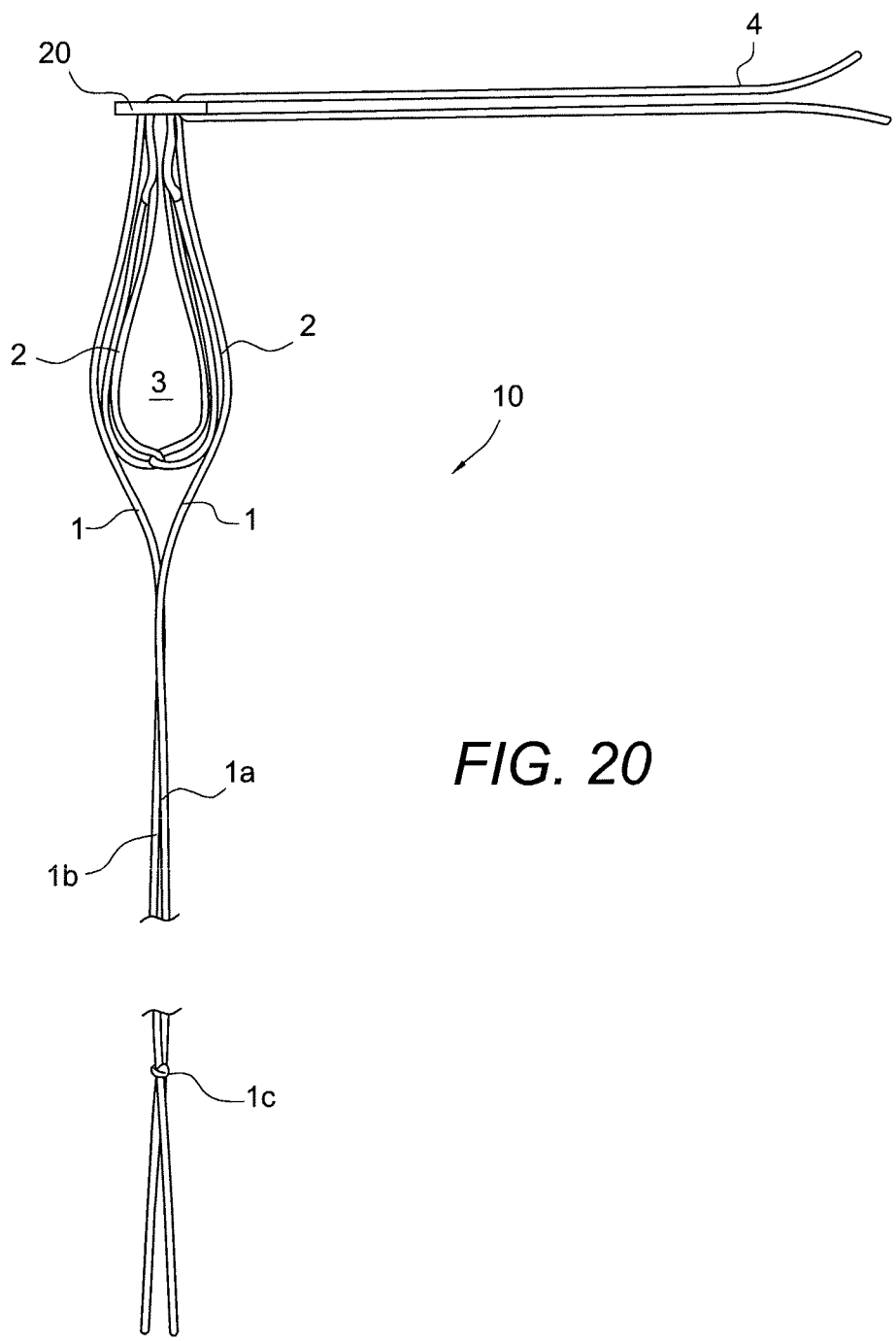
Figure 21:
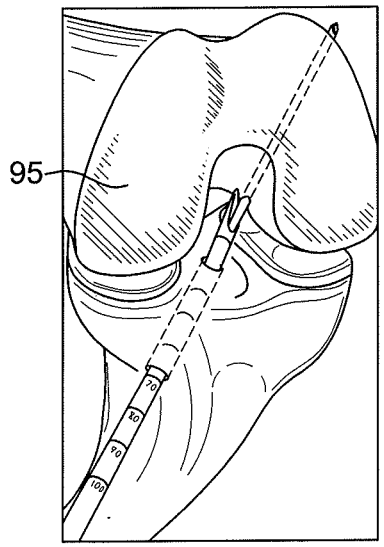
Figure 22:
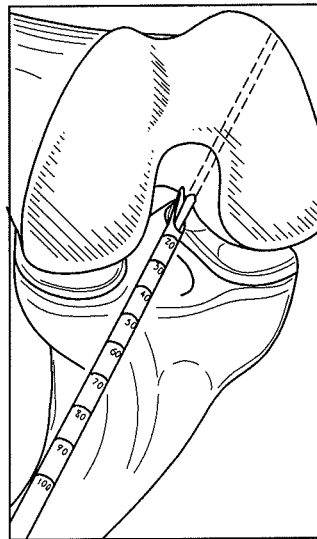
Figure 23:
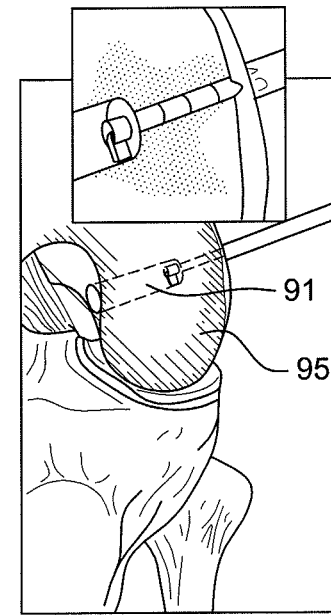
Figure 24:
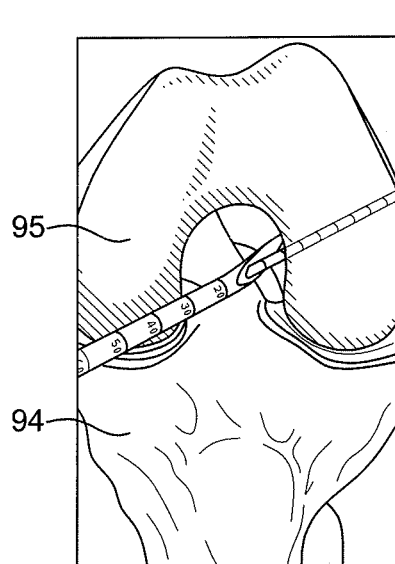

FIGS. 20-40 illustrate a method of ACL reconstruction according to another embodiment of the present invention. In this embodiment, the tissue 80 is looped directly over the adjustable loop 3 of the button/loop construct 10 of the invention. FIG. 20 illustrates construct 10 of FIG. 1 but with flexible ends 1a, 1b connected through a square knot 1c, for example.

Figure 28:
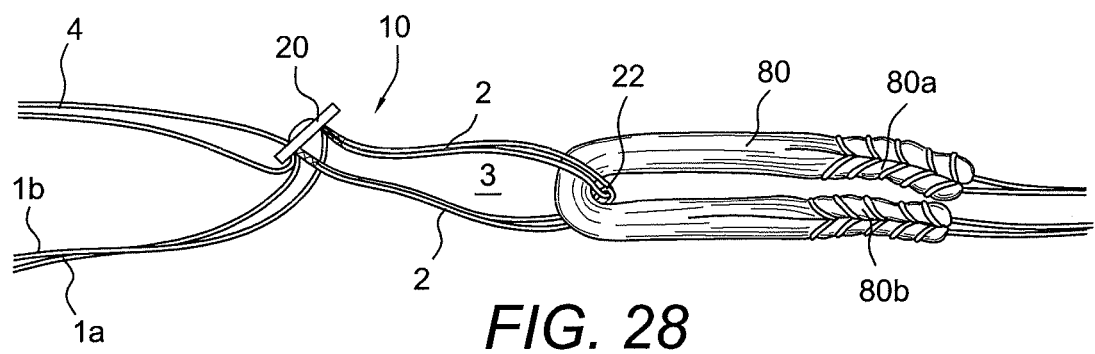
Figure 29:
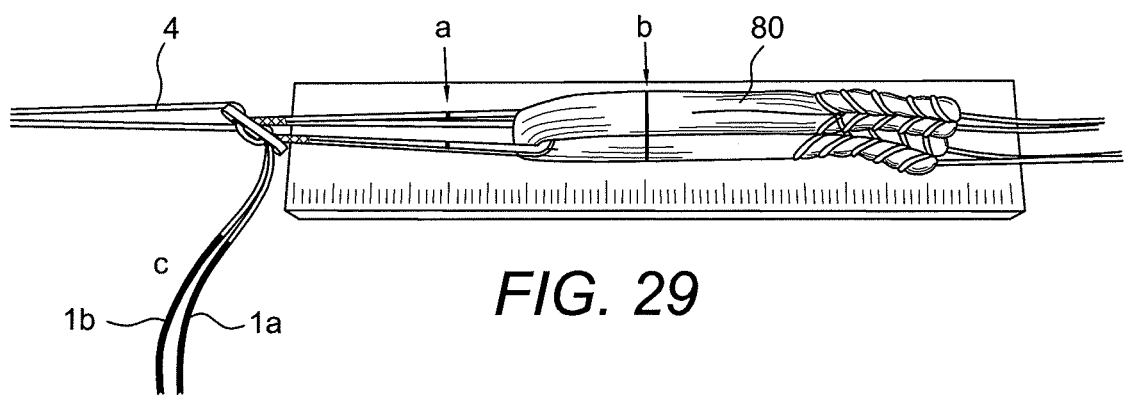

Tissue (graft) 80 is looped over adjustable loop 3 as shown in FIG. 28. Loop shortening strands 1a, 1b of the flexible strand 1 are used to control and adjust the length of the loop 3. FIG. 29 shows the button 20 placed vertically at the end of the Graft Sizing Block. The implant 80 is marked (a) at a distance equal to the intraosseous length from the button 20. The graft 80 is marked (b) at a point equal to the depth of the femoral socket. The first few inches of the loop shortening strands 1a, 1b are marked (c) with a surgical marker to distinguish them from the rest of the implant arthroscopically.

Figure 25:
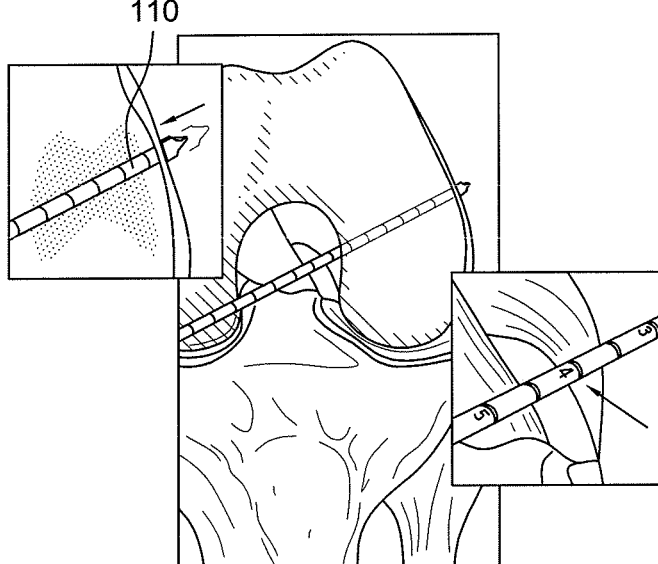

Referring back to FIGS. 21-23, the femoral socket may be drilled transtibially (FIG. 21) or through the medial portal (FIG. 22) or by a retrograde technique using the FlipCutter® (FIG. 23). In the medial portal option (FIGS. 24 and 25), for medial portal and transtibial drilling, a RetroButton® Drill Pin 110 may be used. The intraosseous distance is noted by pulling back on the pin by hand (FIG. 24), until it catches the femoral cortex. The depth marking are read on the pin closest to the femoral notch (FIG. 25).

Figures 26, 27:
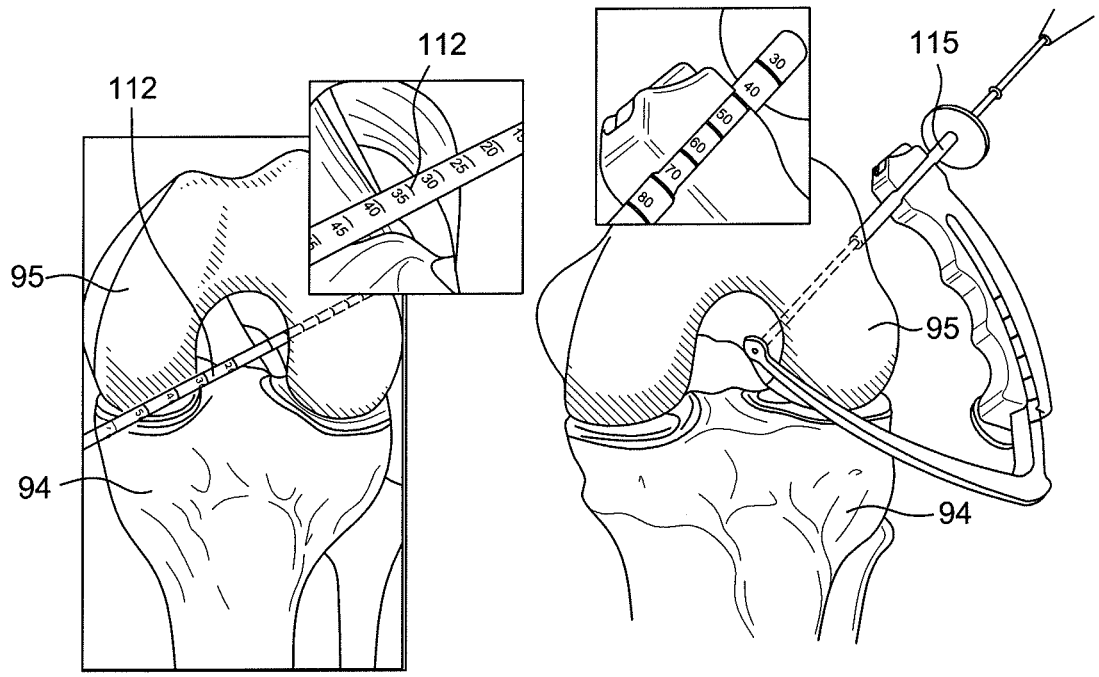

The femur socket 91 is drilled to a depth about equal to the amount of graft desired in the femoral socket, using a Low Profile Reamer 112, for example (FIGS. 26 and 27). After creating the tibial tunnel, the passing suture 4 is brought through the tibia.

If using a FlipCutter 115 (FIG. 27), the intraosseous length off the Drill Sleeve is read. The femur is drilled (by retrograde drilling) a depth equal to the amount of graft desired in the femoral socket 91 (as detailed in the FlipCutter technique). After creating the tibial tunnel 93, the passing suture 4 is brought through the tibia.

Once the implant 80 has been marked (as detailed above with reference to FIGS. 28 and 29), the blue passing suture 4 is passed through the tibia and out the femur (FIGS. 30 and 31). The button 20 is positioned so that the nonlooped side is facing lateral. The button 20 is pulled through the femur until it exits the lateral cortex to achieve fixation (FIG. 31). This is indicated when the mark on the loop reaches the femoral socket opening. No tension should be put on the loop shortening strands until the button has been passed, self-flips, and is fully seated against the cortex, as this could compromise graft advancement.

Referring now to FIGS. 32-34, the marked loop shortening strands 1a, 1b are retrieved from the implant through the medial portal. The graft is advanced and tension is pulled on the loop shortening strands. The graft will be completely seated when the mark on the graft reaches the femoral socket (FIG. 34).

Figures 35, 36, 37:
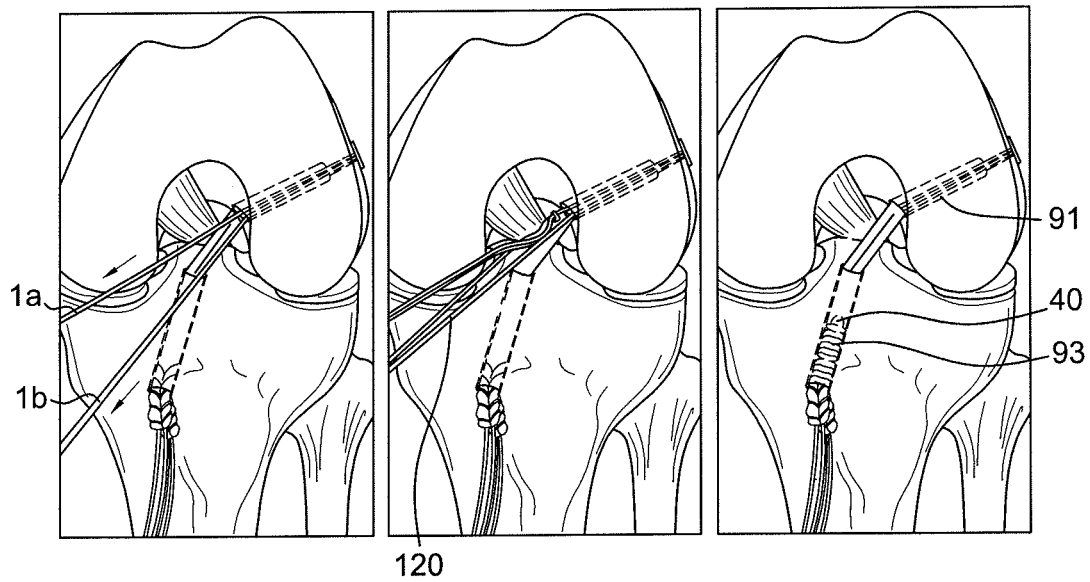

The graft shortening strands 1a, 1b are pulled individually for final graft tensioning (FIGS. 35-37). The graft shortening strands are cut with a cutting instrument 120 (FIG. 36) such as an arthroscopic #2 FiberWire® cutter. The technique proceeds with tibial fixation.

Figure 38:
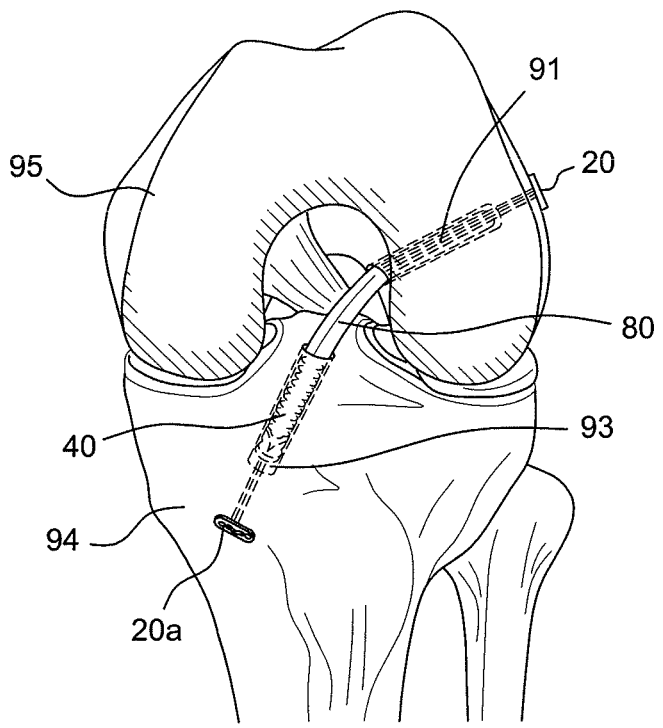

The button/loop construct 10 of FIG. 20 (the wedgeless assembly) is also ideal for all-inside ACL reconstruction (FIG. 38). The adjustability of the implant simplifies graft length determination and allows graft tensioning from the femoral side.

Figure 39:
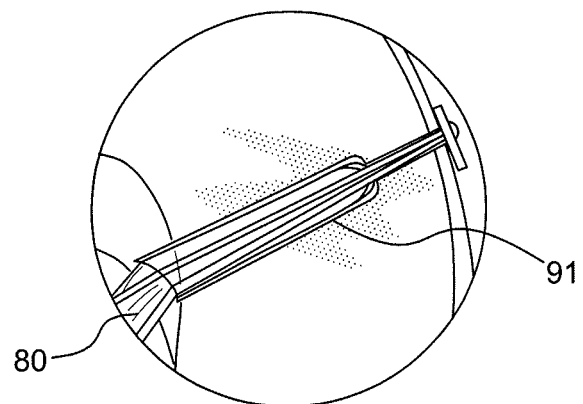
Figure 40:
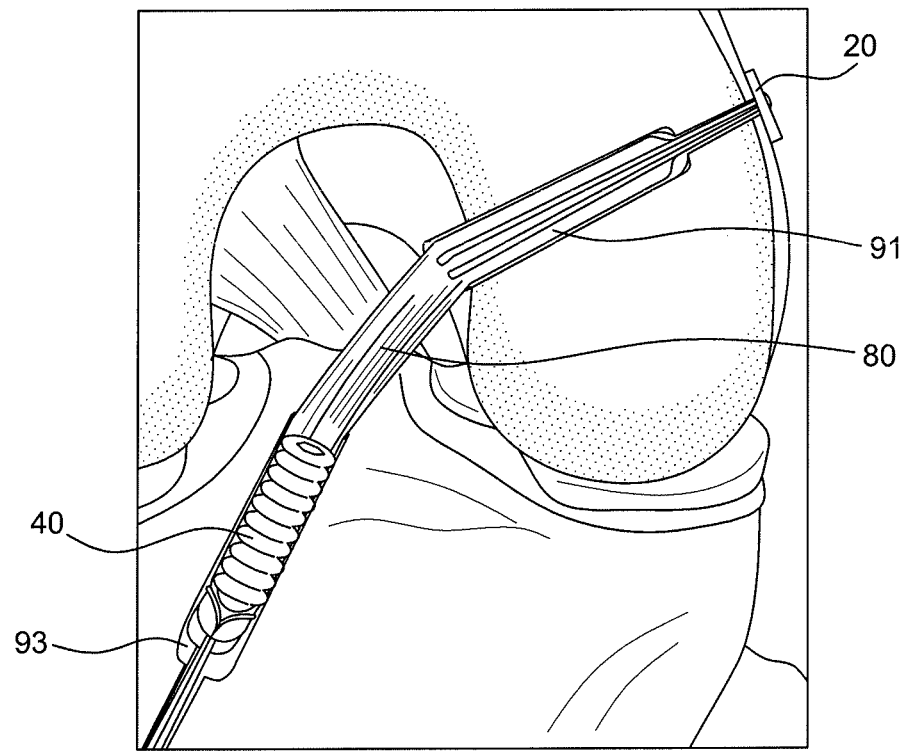

FIG. 39 illustrates a detailed view of the femoral graft of FIG. 38. FIG. 40 illustrates an enlarged view of the final construct of FIG. 38 with tissue (graft) 80 secured within femoral socket 91 and tibia socket 93 by adjustable button/loop construct 10 and an interference device 40.

The adjustable loop of the self-locking adjustable knotless construct 10 is adjustable under tension when the surgeon simply pulls on both ends of the final construct 10 to adjust the length L of the flexible loop and to tighten, therefore, the construct. The button 20 is pulled out of the bone cortex with the passing sutures (which are later discarded) and self-flips onto the cortex immediately upon exiting.

The ACL reconstruction of the present invention offers adjustable cortical fixation for cruciate ligament reconstruction. The four-point knotless fixation resists cyclic displacement and offers maximum loads equal to closed loop devices. The present invention eliminates the need for multiple sized loops and facilitates complete graft fill of short femoral sockets that are common with anatomic ACL drilling.

Although the embodiments above have been described with reference to particular ACL reconstruction techniques, the invention is not limited to these exemplary embodiments. Accordingly, the present invention also contemplates embodiments wherein the self-locking adjustable knotless construct 10 with adjustable loop of the present invention is employed for additional tissue positioning and/or tissue adjustment applications, for example, in fixation of bone to bone (such as small joint applications, or acromioclavicular joint fixation techniques) which employ two fixation devices (for example, two buttons) joined by a continuous suture loop. In these applications, there is no graft supporting device but instead a second button is used in place of the graft supporting device (wedge) 30.

In exemplary embodiments only, the self-locking adjustable knotless construct 10 of the present invention may be employed in a method of bunion repair as described in U.S. Patent Publ. No. 2008/0208252, and/or in a method of Lisfranc repair as described in U.S. Patent Publ. No. 2008/0177302, the disclosures of both of which are incorporated by reference in their entirety herewith (wherein the adjustable suture loop of self-locking adjustable knotless construct 10 would be provided with an additional second button in lieu of the graft contacting device 30). Similarly, the self-locking adjustable knotless construct 10 of the present invention may be employed in a method of fixation of bone to bone as described in U.S. Patent Publ. No. 2007/0179531, the disclosure of which is incorporated by reference in its entirety herewith (wherein the adjustable suture loop of self-locking adjustable knotless construct 10 would be provided with an additional second button in lieu of the graft contacting device 30, so that the adjustable loop extends between a plurality of bone tunnels and secures at least a first bone to a second bone).

In the above-noted exemplary embodiments, the self-locking adjustable knotless construct 10 is not provided with a graft supporting deice (wedge) 30 and, instead of a wedge/plug or screw, a second button can be used (the second button may be round, oblong, and with any number of apertures). The buttons may have a similar or different configuration and they may have at least one hole or aperture (such as button 20 with two apertures, or button 29 with only one aperture). The two buttons/adjustable loop system of the present invention (comprising two buttons with a continuous loop of flexible material having an adjustable length and perimeter) may thus be used for syndesmosis, Lisfranc, and bunion repair, among others, with an adjustable loop construct.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method of ACL reconstruction, comprising:
preparing a first bone tunnel in a femur;
preparing a second bone tunnel in a tibia;
pulling an adjustable button/loop construct through the first bone tunnel and the second bone tunnel, the adjustable button/loop construct including a button and an adjustable loop connected to the button, wherein the adjustable loop includes a first adjustable eyesplice loop and a first free braid strand for shortening the first adjustable eyesplice loop, wherein the first free braid strand extends from the adjustable loop through a first opening of the button;
seating the button against a cortex of the femur; and
after seating the button,
tensioning the first free braid strand to adjust a length of the adjustable loop,
wherein a spliced section of the adjustable loop is at least partially received within the first opening of the button.

2. The method as recited in claim 1, wherein pulling the adjustable button/loop construct includes pulling a passing suture connected to the button of the adjustable button/loop construct.

3. The method as recited in claim 1, wherein tensioning the first free braid strand shortens the first adjustable eyesplice loop.

4. The method as recited in claim 1, comprising looping a graft over the adjustable loop.

5. The method as recited in claim 4, wherein tensioning the first free braid strand secures the graft within the first bone tunnel and the second bone tunnel.

6. The method as recited in claim 4, wherein a spliced section of the adjustable loop is located at a different location from a portion of the adjustable loop over which the graft is looped.

7. The method as recited in claim 1, wherein pulling the adjustable button/loop construct includes passing the adjustable button/loop construct through the second bone tunnel prior to the first bone tunnel.

8. The method as recited in claim 1, wherein the adjustable loop includes a second adjustable eyesplice loop and a second free braid strand for shortening the second adjustable eyesplice loop, wherein the second free braid strand extends from the adjustable loop through a second opening of the button.

9. The method as recited in claim 8, wherein the second opening is a completely separate opening from the first opening.

10. The method as recited in claim 8, wherein the first adjustable eyesplice loop and the second adjustable eyesplice loop are interconnected at an interconnection of the adjustable loop.

11. The method as recited in claim 1, wherein a location at which the first free braid strand is grasped for the tensioning is outside of both the first bone tunnel and the second bone tunnel.

12. The method as recited in claim 1, wherein the first free braid strand extends from the adjustable loop through a bottom surface of the button and exits the button through a top surface of the button.

13. The method as recited in claim 12, wherein the bottom surface and the top surface of the button are substantially flat surfaces.

14. The method as recited in claim 12, wherein, once the button is seated against the cortex, the first free braid strand is accessible laterally outward from the top surface of the button for shortening the first adjustable eyesplice loop.

15. The method as recited in claim 1, wherein the button is an oblong titanium button.

16. A method of ACL reconstruction, comprising:
preparing a first bone tunnel in a femur;
preparing a second bone tunnel in a tibia;
pulling an adjustable button/loop construct through the first bone tunnel and the second bone tunnel, the adjustable button/loop construct including a button and an adjustable loop connected to the button, wherein the adjustable loop includes a first adjustable eyesplice loop and a first free braid strand for shortening the first adjustable eyesplice loop, wherein the first free braid strand extends from the adjustable loop through a first opening of the button;
seating the button against a cortex of the femur; and
after seating the button,
tensioning the first free braid strand to adjust a length of the adjustable loop,
wherein the adjustable loop is comprised of a flexible material having a first end portion and a second end portion, wherein the first end portion is spliced back through the flexible material to form the first adjustable eyesplice loop.

17. A method of ACL reconstruction, comprising:
preparing a first bone tunnel in a femur;
preparing a second bone tunnel in a tibia;
passing an adjustable button/loop construct through the second bone tunnel and then through the first bone tunnel, the adjustable button/loop construct including a button and an adjustable loop connected to the button,
wherein the adjustable loop includes a first adjustable eyesplice loop, a second adjustable eyesplice loop, a first free braid strand for shortening the first adjustable eyesplice loop, and a second free braid strand for shortening the second adjustable eyesplice loop,
wherein the first free braid strand and the second free braid strand extend from the adjustable loop through a bottom surface of the button and exit the button through a top surface of the button,
wherein the first free braid strand extends through a first opening of the button and the second free braid strand extends through a second opening of the button that is completely separate from the first opening;
seating the button against a cortex of the femur;
after seating the button,
tensioning the first free braid strand and the second free braid strand to adjust a length of the adjustable loop; and
looping a graft over the adjustable loop,
wherein a spliced section of the adjustable loop is located at a different location from a portion of the adjustable loop over which the graft is looped.

18. The method as recited in claim 17, wherein the adjustable loop is comprised of a flexible material having a first end portion and a second end portion, wherein the first end portion is spliced back through the flexible material to form the first adjustable eyesplice loop and the second end portion is spliced back through the flexible material to form the second adjustable eyesplice loop.

* * * * *